US006417342B1

(12) United States Patent
Stone et al.

(10) Patent No.: US 6,417,342 B1
(45) Date of Patent: Jul. 9, 2002

(54) MACULAR DEGENERATION DIAGNOSTICS AND THERAPEUTICS

(75) Inventors: Edwin M. Stone, Iowa City; Val C. Sheffield, Coralville, both of IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/248,757

(22) Filed: Feb. 12, 1999

(51) Int. Cl.[7] .............................................. C07H 21/04
(52) U.S. Cl. ................... 536/23.5; 435/252.3; 435/325; 435/320.1
(58) Field of Search .......................... 800/13; 536/23.5; 435/325, 352.3, 320.1

(56) References Cited

FOREIGN PATENT DOCUMENTS

| WO | WO 99/00410 | 1/1999 |
| WO | WO 99/47655 | 9/1999 |

OTHER PUBLICATIONS

Mullins et.al. (Journalmof Clinical Investigation 98(11): S37–S40 See especially p. S39 1996.*
Seamark. Reprod. Fertil. Dev.6: 653–657, see entire document, especially p. 654, col. 2, paragraph 3; and abstract, 1994.*
Moreadith et.al. J. Mol. Med, 1997, p. 214, Summary.*
Rudinger (In Peptide Hormones, J.A. Parsons Ed.. University Park press, Baltimore, Jun. 1996.*
GenBank Accession No. u03877, Apr. 30, 1995.*
Choo et. al. (Nucl. Acids. Res. 15(3): 871–874, Feb. 1987.*
Conlon et.al. (Development 121: 1533–1545, 1995.*
Graff et al.; "Fine Mapping of Best's Macular Dystrophy Localizes the Gene in Close Proximity to but Distinct from the D11S480/ROM1 Loci", Genomics, 24: 425–434 (1994).
Gregory [1] et al.; The Gene Responsible for Autosomal Dominant Doyne's Honeycomb Retinal Dystrophy (DHRD) Maps to Chromosome 2p16.
Ikegawa et al.; "Structure and Chromosomal Assignment of the Human S1–5 Gene (FBNL) That IS Highly Homologous to Fibrillin", Genomics 35: 590–592 (1996).
Kappel et al.; "Regulating Gene Expression in Transgenic Animals", Current Opinion in Biotechnology ,3: 548–553, (1992).
Kilpatrick et al.; "Delivery of a Hammerhead Ribozyme Specifically Down–Relates the Production of Fibrillin –1 by Cultured Dermal Fibroblasts", Human Molecular Genetics , 5(12): 1939–1944 (1996).
Lecka– Czernik et al.; "An Overexpressed Gene Transcript in Senescent and Quiescent Human Fibroblasts Encoding a Novel Protein in the Epidermal Growth Factor–Like Repeat Family Stimulates DNA Synthesis", Molecular and Cellular Biology, 15(1): 120–128(Jan. 1995).

Montgomery and Dietz; "Inhibition of Fibrillin 1 Expression Using U1 snRNA as a Vehicle for the Presentation of Antisense Targeting Sequence", Human Molecular Genetics 6 (4): 519–525 (1997).
Stone et al.; "A Single EFEMP1 Mutation Associated wtih Both Malattia Leventinese and Doyne Honeycomb Retinal Dystrophy", Nature Genetics 22: 199–202 (Jun. 1999).
Viville Stéphane; "Mouse Genetic Manipulation Via Homologous Recombination", Transgenic Animals : generation and Use; Edited by Louis Marie Houdebine, Fance, (1997).
Wall, R.J.; "Transgenic Livestock: Progress and Prospects for the Future", Theriogenology 45: 57–68 (1996).
Partial International Search Report received on Jan. 5, 2001.
Chang, J. G. et al., "Cloning of a Portion of the Chromosomal Gene and cDNA for Human β– Fodrin, the Noneryth-roid Form of β– Spectrin", Genomics 17: 287–293 (1993).
Evans, K. et al., "Clinical Characterization and Genetic Linkage analysis in Doyne's honeycomb Retinal degeneration", Investigative Ophthalmology and Visual Science, vol. 36 No. 4: 890 (1995), Database Biosis No. 98249743.
Graff, C. et al., "Fine Mapping of Best's Macular Dystrophy Localizes the Gene in Close Proximity to But Distinct From the D11S480 / ROM1 Loci", Genomics 24: 425–434 (1994).
Gregory, C. Y. et al., "The Gene Responsible for Autosomal Dominant Doyne's Honeycomb Retinal Dystrophy (DHRD) Maps to Chromosome 2p16", Human Molecular Genetics 5 (7): 1055–1059 (1996).
Héon, E. et al., "Linkage of Autosomal Dominant Radial Drusen (Malattia Leventinese) to Chromosome 2p16– 21)", Archives to Ophthalmology 114 (2): 193–198 (Feb. 1996).
Munier, F. L. et al., "Malattia Levantinese: exclusion of Known Disease Causing Gene Associated with Macular Dystrophies", American Journal of Human Genetics, 57(4): 333 (1995).
Small, K. W. et al., "North Carolina macular dystrophy (MCDR1). A review and refined mapping to 6q14–q 16.2", Opthalmic Paedriatics and Genetics 14(4): 143– 150 (1993).
Weber, B. H. F., "Die Genetik der Makuladegenerationen", Klinische Monatsblatter fur Augenheilkunde, vol. 210 No. 1, pp. 9–17 (Jan. 1, 1997).
Zhang, K. et al., "Genetics and Molecular Studies of Macular Dystrophies : Recent Developments", Survey of Ophthalmology, 40 (1): 51– 61 (1995).

* cited by examiner

*Primary Examiner*—James Ketter
*Assistant Examiner*—Richard Schnizer
(74) *Attorney, Agent, or Firm*—Needle & Rosenberg, P.C.

(57) ABSTRACT

Therapeutics and diagnostics based on the identification of genetic mutations, which cause Macular Degeneration (MD) is disclosed.

6 Claims, 8 Drawing Sheets

MACULAR DEGENERATION DIAGNOSTICS AND THERAPEUTICS

1. BACKGROUND OF THE INVENTION

Figure 1A:
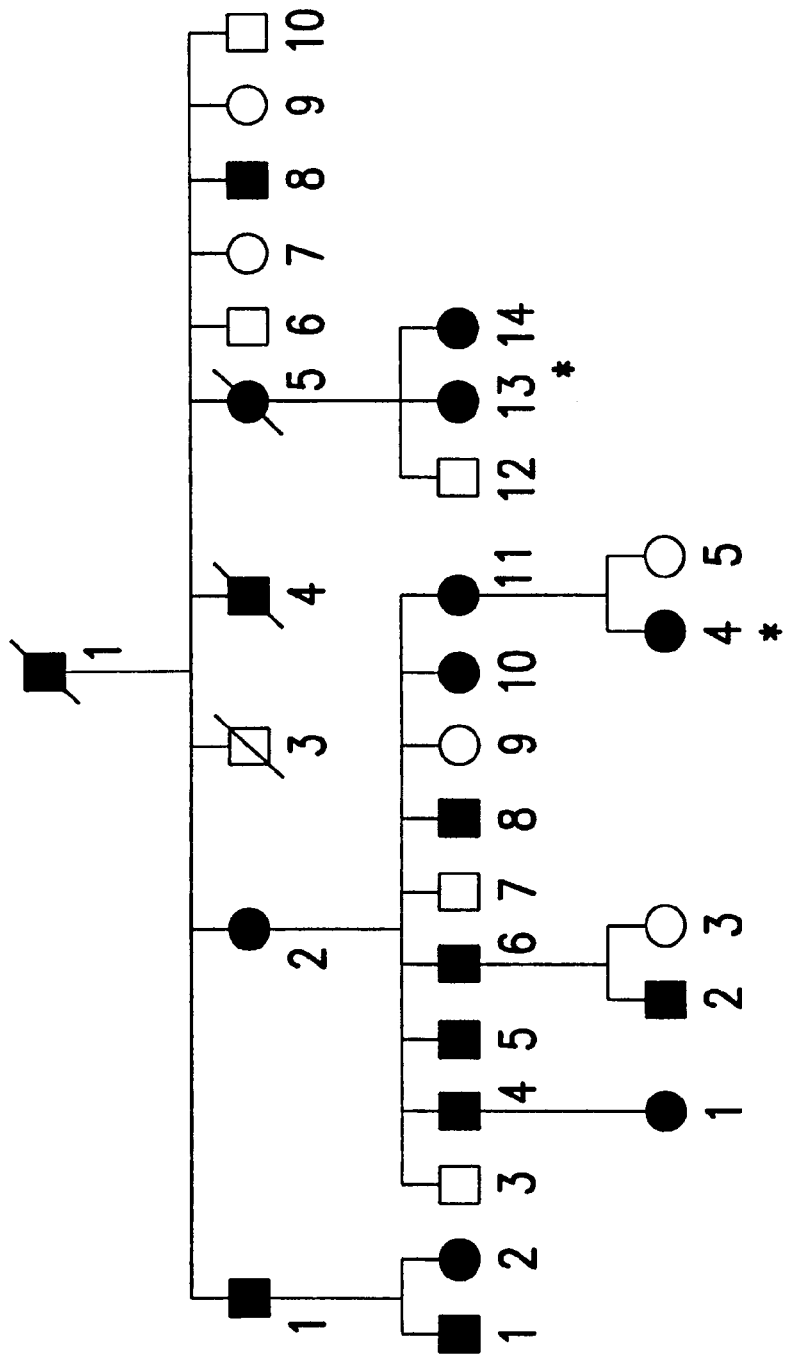
Figure 1B:
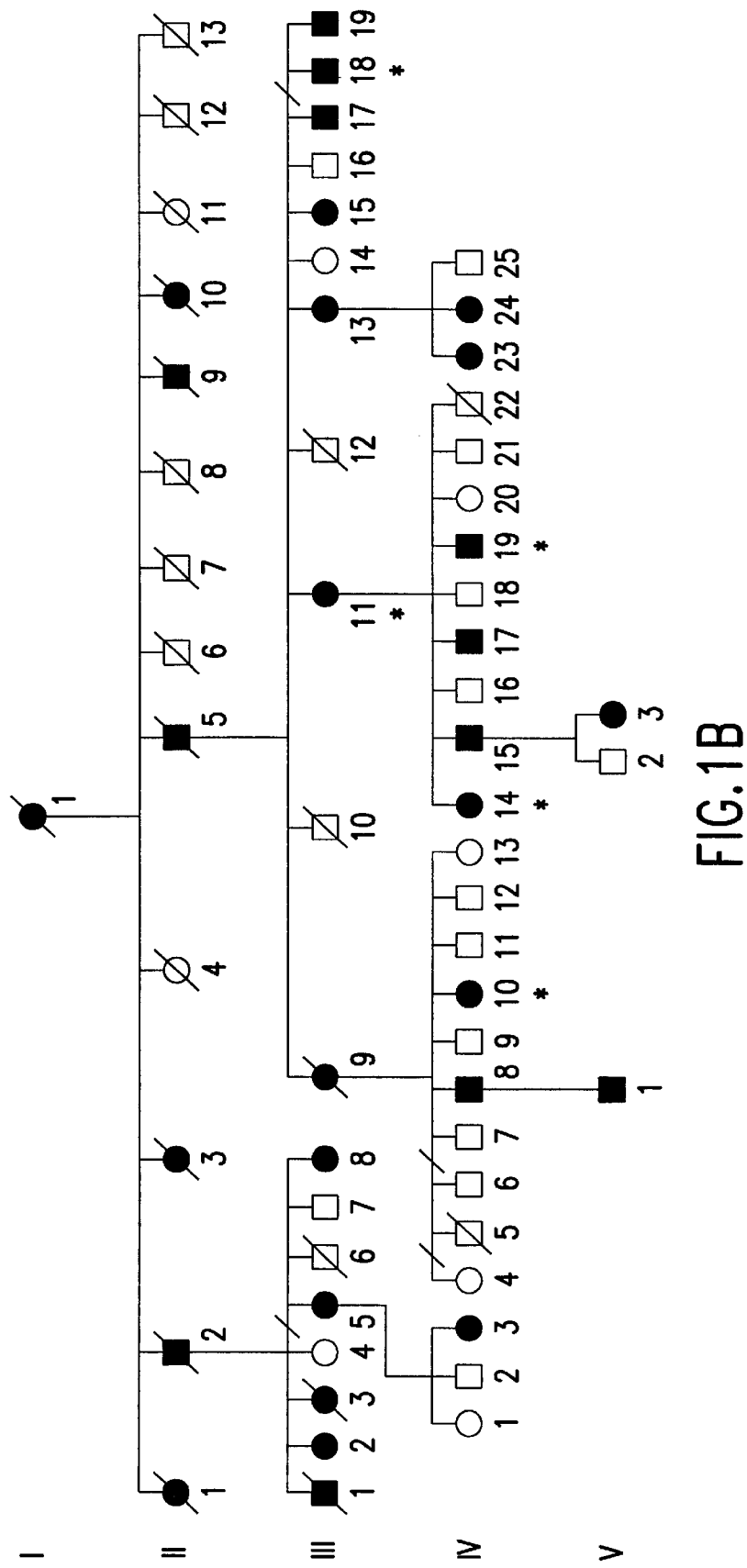
Figure 1C:
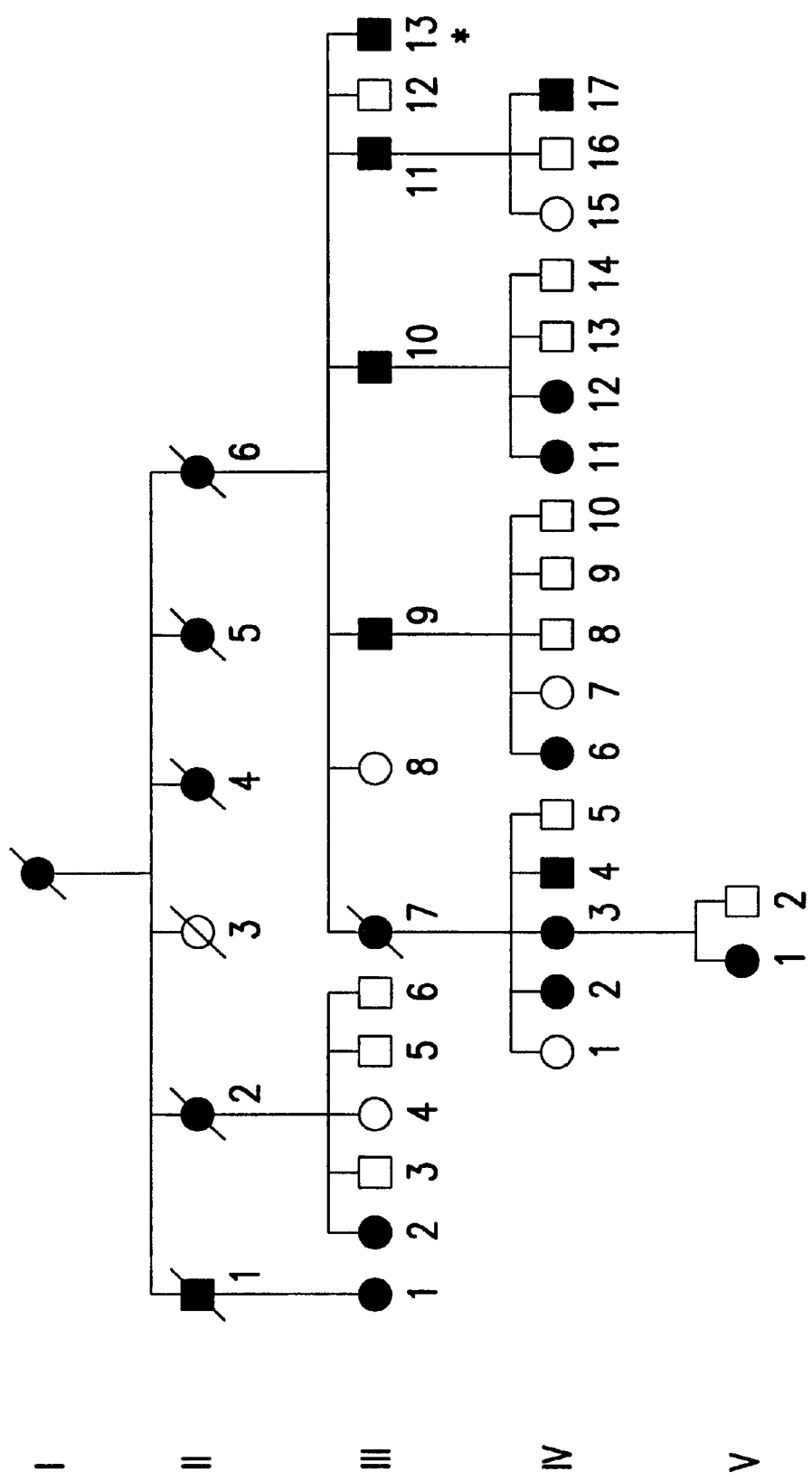
Figure 1D:
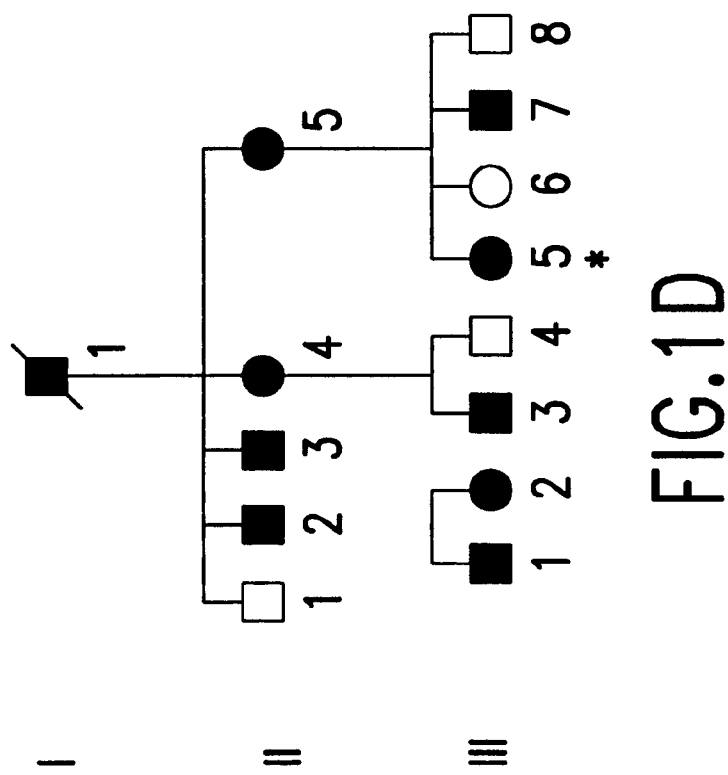
Figure 1E:
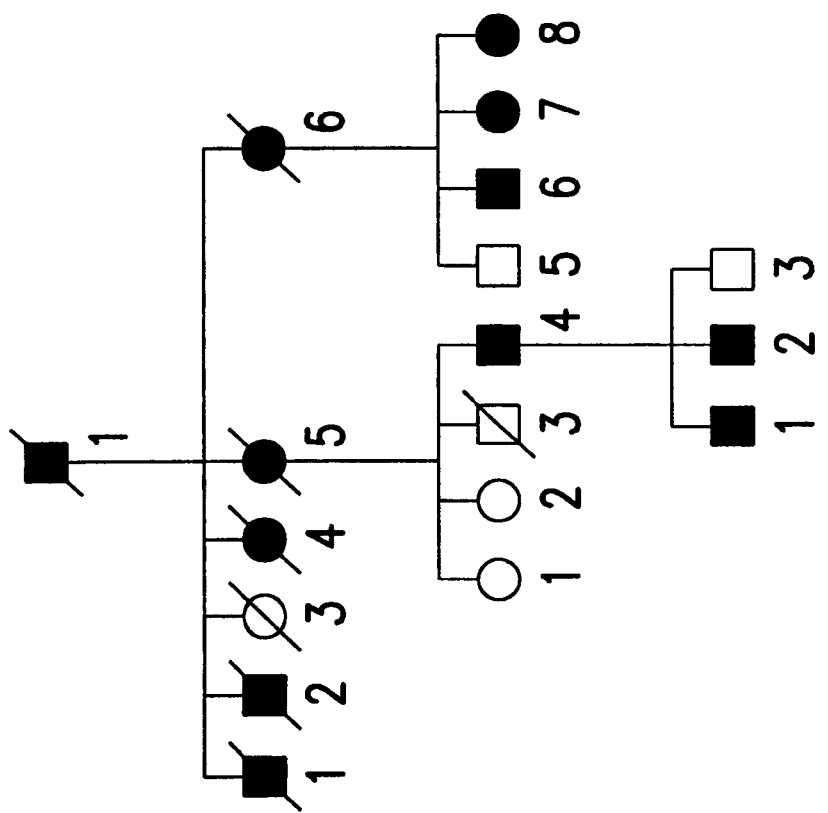

Macular degeneration is a clinical term that is used to describe a variety of diseases that are all characterized by a progressive loss of central vision associated with abnormalities of Bruch's membrane and the retinal pigment epithelium. These disorders include very common conditions that affect older patients (age related macular degeneration or AMD) as well as rarer, earlier-onset dystrophies that in some cases can be detected in the first decade of life[1-18]. The genes associated with some of these dystrophies have been mapped,[5-14] and in three cases, blue-cone monochromasy,[15] pattern dystrophy,[16,17] and Sorsby fundus dystrophy,[18] actually identified. However, none of the latter genes has been found to be responsible for a significant fraction of typical late-onset macular degeneration.

In developed countries, AMD is the most common cause of legal blindness in older patients.[19] The hallmark of this condition is the presence of drusen, which are ophthalmoscopically visible, yellow-white hyaline excrescences of Bruch's membrane. In some families, drusen are heritable in an autosomal dominant fashion.

In 1875, Hutchinson and Tay published a paper entitled "Symmetrical Central Choroido-Retinal Disease Occurring in Senile Persons".[20] This paper includes one of the first descriptions of the constellation of clinical findings now known as age related macular degeneration (AMD). Specifically, three of the ten patients in the report were sisters affected with whitish spots (now referred to as drusen) in the macula. In 1899, Doyne[21] reported a similar disorder in which the abnormal spots were nearly confluent such that the macula had a "honeycomb" appearance. Histopathologic examination of one of Doyne's patients[22] revealed the abnormalities to be hyaline thickenings of Bruch's membrane. In 1925, Vogt[23] published the first description of the ophthalmoscopic appearance of a form of familial drusen that had been observed in patients living in the Leventine valley in the Ticino canton of southern Switzerland. Klainguti[24] fully characterized this condition in 1932 and demonstrated its autosomal dominant inheritance. This disorder eventually became known as malattia leventinese (i.e., Leventine disease). In 1948, Waardenburg[25] stated that there was little reason to make a distinction between malattia leventinese and the condition described by Doyne. This position was strengthened when Forni and Babel[26] found that the histopathologic features of malattia leventinese were indistinguishable from those of Doyne's honeycomb choroiditis. Piguet, Haimovici and Bird[27] recently reviewed the history of these conditions and also pointed out that the drusen in families with malattia leventinese are frequently distributed in a radical pattern (see also FIGS. 2 and 3). Choroidal neovascularization is uncommon in patients with radial drusen but does occur.[27] Although originally recognized in Switzerland, families affected with autosomal dominant radial drusen have been identified in Czechoslovakia,[28,29] and the United States.[30]

Currently, there is no therapy that is capable of significantly slowing the degenerative progression of AMD, and treatment is limited to laser photocoagulation of the subretinal neovascular membranes that occur in 10–15% of affected patients.

2. SUMMARY OF THE INVENTION

In one aspect the invention features methods for diagnosing a subject with macular degeneration or with a predisposition for developing macular degeneration. In a preferred embodiment, the diagnostic methods utilize a set of primers and/or probes for amplifying and/or detecting regions of the macular degeneration causing gene, and means for analyzing the macular degeneration causing gene for differences (mutations) from the normal coding sequence. For example, the MD causative mutation can be detected by any of a variety of available techniques, including: 1) performing a hybridization reaction between a nucleic acid sample and a probe that is capable of hybridizing to the allele; 2) sequencing at least a portion of the allele; or 3) determining the electrophoretic mobility of the allele or fragments thereof (e.g., fragments generated by endonuclease digestion). The allele can optionally be subjected to an amplification step prior to performance of the detection step. Preferred amplification methods are selected from the group consisting of: the polymerase chain reaction (PCR), the ligase chain reaction (LCR), strand displacement amplification (SDA), cloning, and variations of the above (e.g. RT-PCR and allele specific amplification). Oligonucleotides necessary for amplification may be selected from anywhere in the IL-1 gene loci, either flanking the marker of interest (as required for PCR amplification) or directly overlapping the marker (as in ASO hybridization). The DNA in the human IL-1 region has been mapped, and oligonucleotides for primers can easily be selected with a commercially available primer selection program. In a particularly preferred embodiment, the sample is hybridized with a set of primers, which hybridize 5' and 3' in a sense or antisense sequence to the mutation, and is subjected to a PCR amplification. In a preferred embodiment, the MD causative mutation results in the following amino acid substitutions to the FBNL protein: 345Arg>Trp and 362 Arg>Gln.

In another embodiment, the diagnostic methods employ antibodies to a macular degeneration causing protein (i.e. a protein encoded by the macular degeneration gene) in an immunoassay procedure to detect the presence of a macular degeneration causing protein in a subject's bodily fluid (e.g. tears).

In another aspect, the invention features kits for performing the above-described assays. The kit can include sample collection means and a means for determining whether a subject carries an MD causative mutation. The kit may also comprise control samples, either negative or positive, or standards.

Information obtained using the assays and kits described herein is useful, for example, for identifying presymptomatic individuals, who are at risk for developing MD, e.g. based on family history. If the diagnosis is negative, the individual will not need to worry about the potential development of the disease over time. If the diagnosis is positive, steps may be taken to prevent or ameliorate the effects of the disease before damage, such as loss of vision, occurs. In addition, the information can allow a more customized approach to prolonging the onset or treating the symptoms associated with MD. For example, this information can enable a doctor to: 1) more effectively prescribe a drug that will address the molecular basis of MD in the subject; and/or 2) better determine the appropriate drug and dosage of a particular drug for the particular subject.

In yet a further aspect, the invention features methods for treating or preventing the development of MD in a subject by administering to the subject, a pharmaceutically effective amount of an MD therapeutic of the invention. In one embodiment, the MD therapeutic is a macular degeneration correcting gene or protein (i.e. a "normal" FBNL or related gene or protein (e.g. fibulin 1 or fibulin 2), which corresponds to a mutated gene or defective protein that causes the development of macular degeneration). In another embodiment, the MD therapeutic is an antagonist of the mutant protein activity or an agonist of the wildtype protein activity.

The instant disclosed MD therapeutics correct the biochemical defect resulting in disease. Therefore the instant disclosed therapies offer a major advance over current treatments (e.g. laser photocoagulation of the subretinal neovascular membranes that only occur in 10–15% of affected patients.

In still another aspect, the invention provides in vitro and in vivo assays for screening test compounds to identify MD therapeutics. In another embodiment, the invention features transgenic non-human animals and their use, for example in identifying MD therapeutics.

Other features and advantages will be readily apparent from the following detailed description and claims.

3. BRIEF DESCRIPTION OF THE DRAWINGS

FIGS. 1A–1E are graphic representations of the family pedigrees involved in the studies described in Example 1. Individuals found to be clinically affected with radial drusen are represented by black symbols while unaffected individuals are depicted with open symbols. Individuals that are deceased are marked with a slash. All living affected patients shown were included in the linkage analysis except those marked with an asterisk. The affection status of the deceased patients and of the patients marked with an asterisk was obtained historically.

Figure 2:
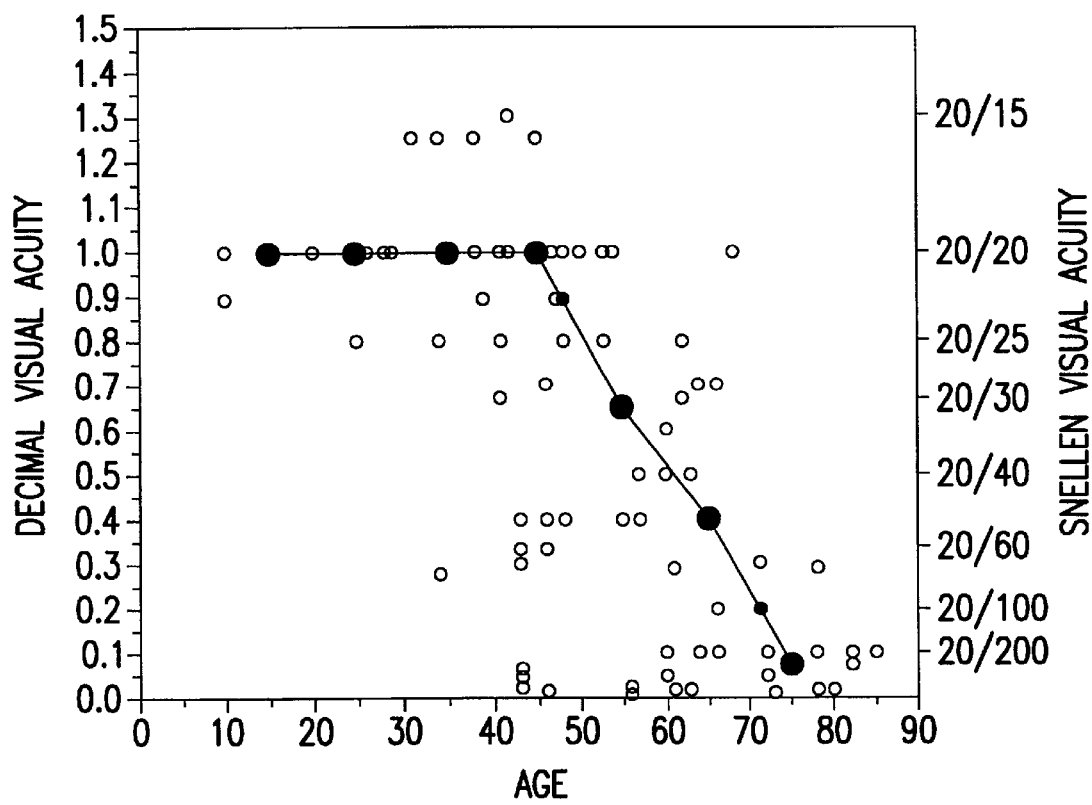

FIG. 2 is a graph plotting the decline of visual acuity of macular degeneration patients with age. Each open symbol represents the visual acuity of an affected eye at one point in time. The acuity is expressed in decimal notation ($20/20=1.0$; $20/200=0.1$). Each heavy closed symbol represents the median visual acuity for all eyes in a single decade of life. These median acuities are plotted at the centers of the relevant decades (e.g., 25 for the decade from age 20 through 29).

Figure 3:
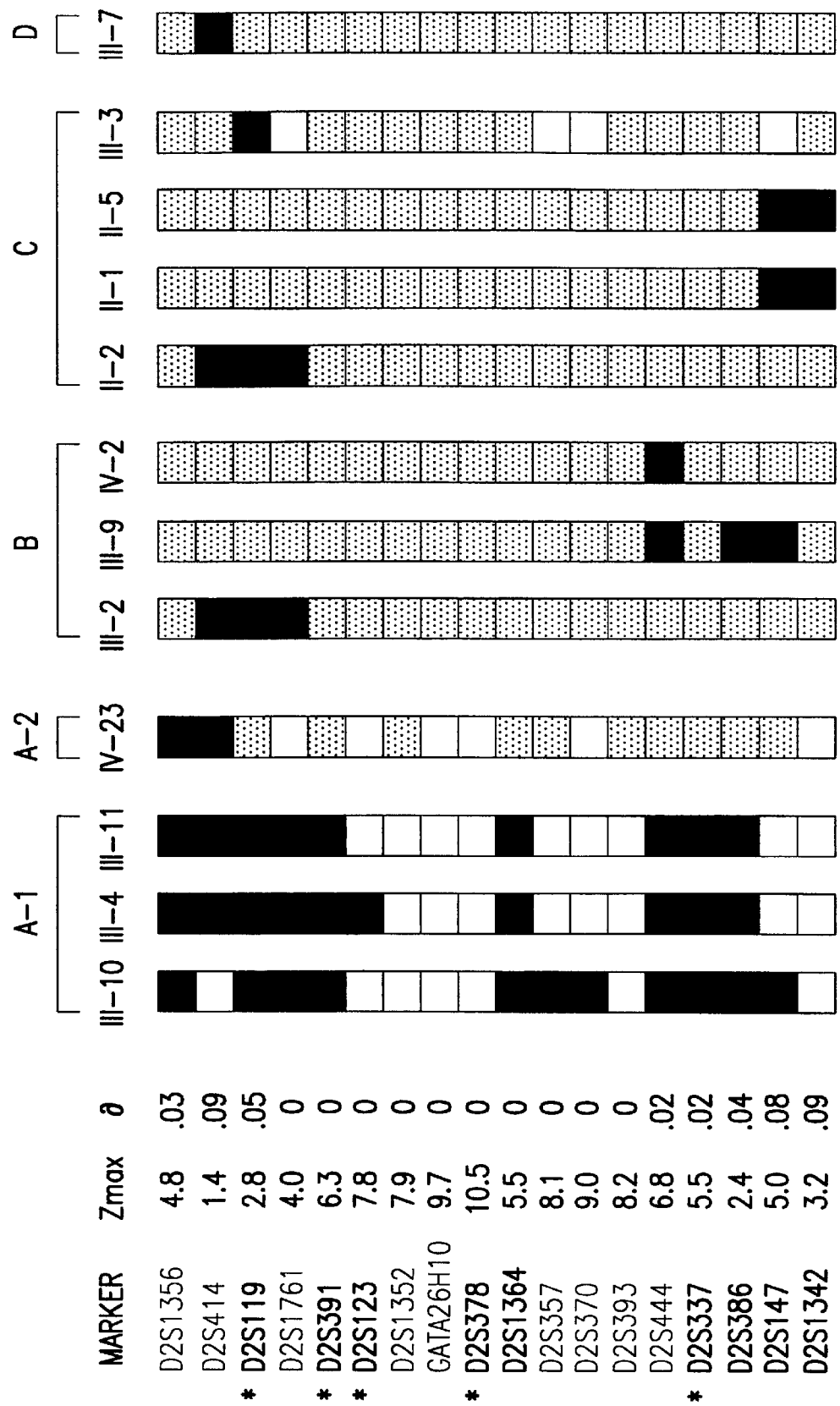

FIG. 3 shows two point linkage data and analysis of recombinant individuals. Eighteen genetic markers from the short arm of chromosome 2 are listed on the left of the figure with the most centromeric marker at the bottom. Dots indicate markers that could be positioned on the map in an order that was greater than $10^8$ times more likely than the next most likely order. Bold type (without a dot) indicates that a marker could be ordered with greater than 1000:1 odds while plain type indicates less than 1000:1 odds for the marker order. The maximum lod score (Zmax) for all four families combined is given for each marker as well as the recombination frequency at which Zmax occurred (theta hat). Each vertical group of boxes depicts the haplotypic data from a clinically affected individual who exhibits a recombination event near the linked interval. The family designations and pedigree numbers correspond to those in FIG. 1. A black box indicates that during the meiosis that gave rise to the individual, an informative recombination event occurred between the marker and the disease gene. A white box indicates that the meiosis is informative (at least with respect to the affected parent) and that no recombination occurred between the disease gene and the marker. A gray box indicates that the meiosis is uninformative at that marker. The recombination events summarized in this figure suggest that the disease-causing mutations lie within the interval bounded by D2S1761 and D2S4444.

Figure 4:
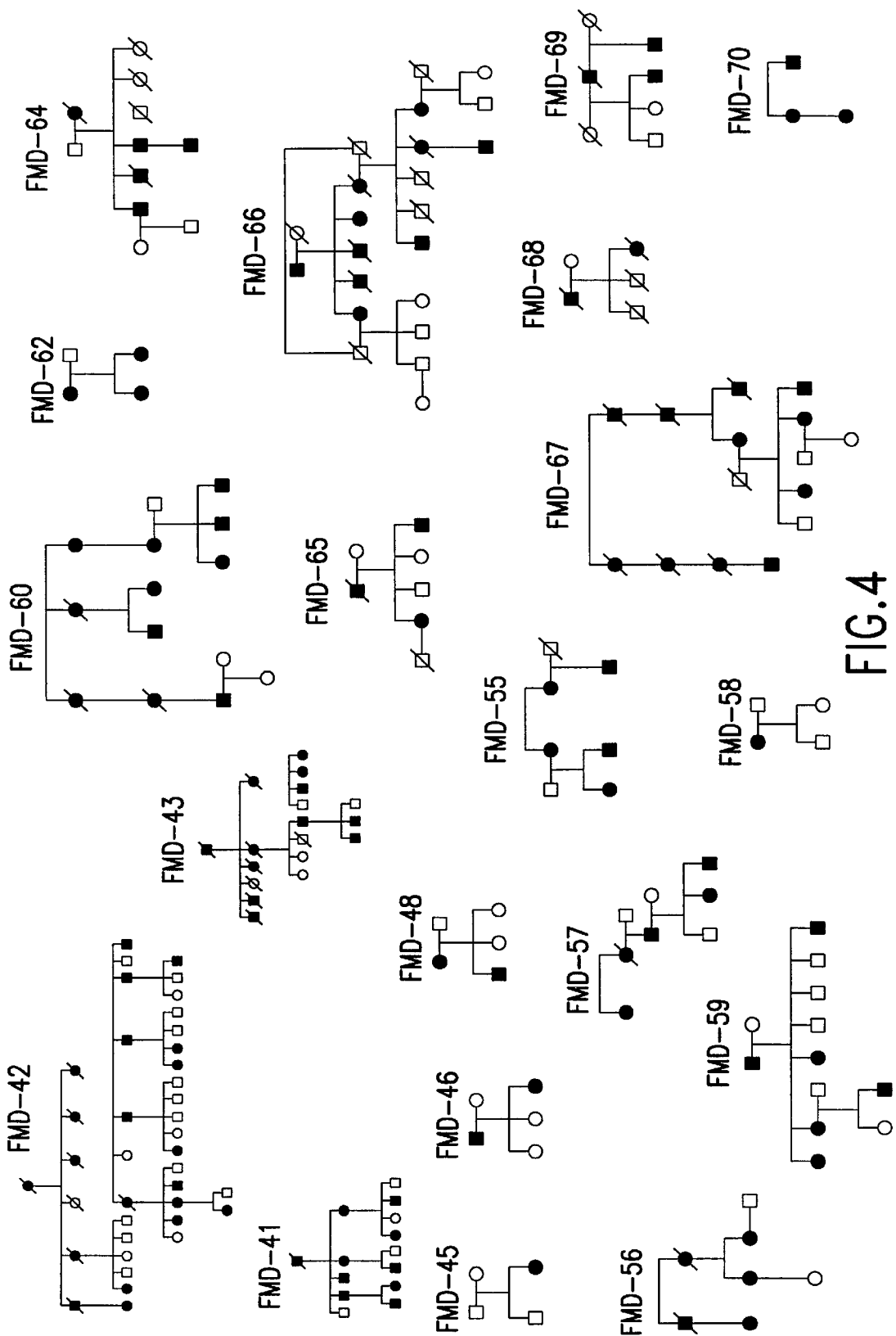

FIG. 4 shows the results of an analysis of twenty Swiss Malattia Leventinese families, which has haplotypically narrowed the interval to approximately 1 cM defined by markers D2S2352-D2S1364.

4. DETAILED DESCRIPTION

4.1 Definitions

For convenience, the meaning of certain terms and phrases employed in the specification, examples, and appended claims are provided below.

The term "an aberrant activity", as applied to an activity of a polypeptide such as FBNL, refers to an activity which differs from the activity of the wild-type or native polypeptide or which differs from the activity of the polypeptide in a healthy subject. An activity of a polypeptide can be aberrant because it is stronger than the activity of its native counterpart. Alternatively, an activity can be aberrant because it is weaker or absent relative to the activity of its native counterpart. An aberrant activity can also be a change in an activity. For example an aberrant polypeptide can interact with a different target peptide or polypeptide. A cell can have an aberrant FBNL activity due to overexpression or underexpression of a wild-type or mutant FBNL polypeptide.

"Biological activity" or "bioactivity" or "activity" or "biological function", which are used interchangeably, for the purposes herein means an effector or antigenic function that is directly or indirectly performed by an FBNL polypeptide (whether in its native or denatured conformation), or by any subsequence thereof. Biological activities include binding to a target peptide. An FBNL bioactivity can be modulated by directly affecting the binding between an FBNL and an FBNL binding partner. Alternatively, an IL-1 bioactivity can be modulated by modulating the level of an FBNL polypeptide, such as by modulating expression of an FBNL gene.

As used herein the term "bioactive fragment of an FBN-Lpolypeptide" refers to a fragment of a full-length FBNL polypeptide, wherein the fragment specifically mimics or antagonizes the activity of a wild-type FBNL polypeptide. The bioactive fragment preferably is a fragment capable of interacting with an FBNL binding partner.

"Cells," "host cells" or "recombinant host cells" are terms used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A "chimeric protein" or "fusion protein" is a fusion of a first amino acid sequence encoding one of the subject polypeptides with a second amino acid sequence defining a domain (e.g. polypeptide portion) foreign to and not substantially homologous with any domain of one of the polypeptides. A chimeric protein may present a foreign domain which is found (albeit in a different protein) in an organism which also expresses the first protein, or it may be an "interspecies", "intergenic", etc. fusion of protein structures expressed by different kinds of organisms.

"Complementary" sequences as used herein refer to sequences which have sufficient complementarily to be able to hybridize, forming a stable duplex.

The terms "control" or "control sample" refer to any sample appropriate to the detection technique employed. The control sample may contain the products of the allele detection technique employed or the material to be tested.

Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested.

The phrases "disruption of the gene" and "targeted disruption" or any similar phrase refers to the site specific interruption of a native DNA sequence so as to prevent expression of that gene in the cell as compared to the wild-type copy of the gene. The interruption may be caused by deletions, insertions or modifications to the gene, or any combination thereof.

A "delivery complex" shall mean a targeting means (e.g. a molecule that results in higher affinity binding of a gene, protein, polypeptide or peptide to a target cell surface and/or increased cellular uptake by a target cell). Examples of targeting means include: sterols (e.g. cholesterol), lipids (e.g. a cationic lipid, virosome or liposome), viruses (e.g. adenovirus, adeno-associated virus, and retrovirus) or target cell specific binding agents (e.g. ligands recognized by target cell specific receptors). Preferred complexes are sufficiently stable in vivo to prevent significant uncoupling prior to internalization by the target cell. However, the complex is cleavable under appropriate conditions within the cell so that the gene, protein, polypeptide or peptide is released in a functional form.

As is well known, genes for a particular polypeptide may exist in single or multiple copies within the genome of an individual. Such duplicate genes may be identical or may have certain modifications, including nucleotide substitutions, additions or deletions, which all still code for polypeptides having substantially the same activity. The term "DNA sequence encoding a polypeptide" may thus refer to one or more genes within a particular individual. Moreover, certain differences in nucleotide sequences may exist between individual organisms, which are called alleles. Such allelic differences may or may not result in differences in amino acid sequence of the encoded polypeptide yet still encode a protein with the same biological activity.

An "FBNL" gene or protein refers to a "fibrillin like" gene or protein that encodes an extracellular matrix protein. cDNA encoding a portion of the protein is posted in GenBank under accession number UO3877. FBNL includes genes, proteins and portions thereof, which are substantially homologous in structure and function, including fibulin (1 and 2), Fibrillin, nidogen, notch, protein S and Factor IX.

As used herein, the term "gene" or "recombinant gene" refers to a nucleic acid molecule comprising an open reading frame encoding one of the polypeptides of the present invention, including both exon and (optionally) intron sequences. A "recombinant gene" refers to nucleic acid molecule encoding a polypeptide and comprising protein-encoding exon sequences, though it may optionally include intron sequences which are derived from a chromosomal gene. Exemplary recombinant genes encoding the subject polypeptides are represented in the appended Sequence Listing. The term "intron" refers to a DNA sequence present in a given gene which is not translated into protein and is generally found between exons.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, though preferably less than 25% identity, with one of the sequences of the present invention.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

The term "interact" as used herein is meant to include detectable interactions between molecules, such as can be detected using, for example, a yeast two hybrid coimmunoprecipitation assay. The term interact is also meant to include "binding" interactions between molecules. Interactions may be protein-protein or protein-nucleic acid in nature.

The term "isolated" as used herein with respect to nucleic acids, such as DNA or RNA, refers to molecules separated from other DNAs or RNAs, respectively, that are present in the natural source of the macromolecule. For example, an isolated nucleic acid encoding one of the subject polypeptides preferably includes no more than 10 kilobases (kb) of nucleic acid sequence which naturally immediately flanks the gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides. A "knock-in" transgenic animal refers to an animal that has had a modified gene introduced into its genome and the modified gene can be of exogenous or endogenous origin.

A "knock-out" transgenic animal refers to an animal in which there is partial or complete suppression of the expression of an endogenous gene (e.g, based on deletion of at least a portion of the gene, replacement of at least a portion of the gene with a second sequence, introduction of stop codons, the mutation of bases encoding critical amino acids, or the removal of an intron junction, etc.).

A "knock-out construct" refers to a nucleic acid sequence that can be used to decrease or suppress expression of a protein encoded by endogenous DNA sequences in a cell.

"Linkage disequilibrium" refers to co-inheritance of two alleles at frequencies greater than would be expected from the separate frequencies of occurrence of each allele in a given control population. The expected frequency of occurrence of two alleles that are inherited independently is the frequency of the first allele multiplied by the frequency of the second allele. As used herein, the term "linkage disequilibrium" also refers to linked sequences. Alleles that co-occur at expected frequencies are said to be in "linkage equilibrium" or "not linked." When referring to allelic patterns that are comprised of more than one allele, a first allelic pattern is in linkage disequilibrium with a second allelic pattern if all the alleles that comprise the first allelic pattern are in linkage disequilibrium with at least one of the alleles of the second allelic pattern.

"MD" or "Macular Degeneration" is a clinical term that is used to describe a variety of diseases that are all characterized by a progressive loss of central vision associated with abnormalities of Bruch's membrane and the retinal pigment epithelium. These disorders include very common conditions that affect older patients (age related macular degeneration or AMD) as well as rarer, earlier-onset dystrophies that in some cases can be detected in the first few decades of life. Examples include Malattia Leventinese and Doyne's Macular Dystrophy.

An "MD therapeutic" refers to an agent that is useful in treating or preventing the development of a Macular Degeneration. Examples include genes, proteins (e.g. glycosylated or unglycosylated protein, polypeptide or protein) or other organic or inorganic molecules (e.g. small molecules) that interfere with or compensate for the biochemical events that are causative of MD.

A "mutated gene" or "mutation" or "functional mutation" refers to an allelic form of a gene, which is capable of altering the phenotype of a subject having the mutated gene relat a subject which does not have the mutated gene. The altered phenotype caused by a mutation can be corrected or compensated for by certain agents. If a subject must be homozygous for this mutation to have an altered phenotype, the mutation is said to be recessive. If one copy of the mutated gene is sufficient to alter the phenotype of the subject, the mutation is said to be dominant. If a subject has one copy of the mutated gene and has a phenotype that is intermediate between that of a homozygous and that of a heterozygous subject (for that gene), the mutation is said to be co-dominant.

The "non-human animals" of the invention include mammalians such as rodents, non-human primates, sheep, dog, cow, chickens, amphibians, reptiles, etc. Preferred non-human animals are selected from the rodent family including rat and mouse, most preferably mouse. The term "chimeric animal" is used herein to refer to animals in which the recombinant gene is found, or in which the recombinant is expressed in some but not all cells of the animal. The term "tissue-specific chimeric animal" indicates that one of the recombinant genes is present and/or expressed or disrupted in some tissues but not others.

As used herein, the term "nucleic acid" refers to polynucleotides such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

As used herein, the term "promoter" means a DNA sequence that regulates expression of a selected DNA sequence operably linked to the promoter, and which effects expression of the selected DNA sequence in cells. The term encompasses "tissue specific" promoters, i.e. promoters, which effect expression of the selected DNA sequence only in specific cells (e.g. cells of a specific tissue). The term also covers so-called "leaky" promoters, which regulate expression of a selected DNA primarily in one tissue, but cause expression in other tissues as well. The term also encompasses non-tissue specific promoters and promoters that constitutively express or that are inducible (i.e. expression levels can be controlled).

The terms "protein", "polypeptide" and "peptide" are used interchangeably herein when referring to a gene product.

The term "recombinant protein" refers to a polypeptide of the present invention which is produced by recombinant DNA techniques, wherein generally, DNA encoding a polypeptide is inserted into a suitable expression vector which is in turn used to transform a host cell to produce the heterologous protein. Moreover, the phrase "derived from", with respect to a recombinant gene, is meant to include within the meaning of "recombinant protein" those proteins having an amino acid sequence of a native protein, or an amino acid sequence similar thereto which is generated by mutations including substitutions and deletions (including truncation) of a naturally occurring form of the protein.

"Small molecule" as used herein, is meant to refer to a composition, which has a molecular weight of less than about 5kD and most preferably less than about 4kD. Small molecules can be nucleic acids, peptides, peptidomimetics, carbohydrates, lipids or other organic or inorganic molecules.

As used herein, the term "specifically hybridizes" or "specifically detects" refers to the ability of a nucleic acid molecule of the invention to hybridize to at least approximately 6, 12, 20, 30, 50, 100, 150, 200, 300, 350, 400 or 425 consecutive nucleotides.

"Transcriptional regulatory sequence" is a generic term used throughout the specification to refer to DNA sequences, such as initiation signals, enhancers, and promoters, which induce or control transcription of protein coding sequences with which they are operably linked. In preferred embodiments, transcription of one of the recombinant genes is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences which control transcription of the naturally-occurring forms of proteins.

As used herein, the term "transfection" means the introduction of a nucleic acid, e.g., an expression vector, into a recipient cell by nucleic acid-mediated gene transfer. "Transformation", as used herein, refers to a process in which a cell's genotype is changed as a result of the cellular uptake of exogenous DNA or RNA, and, for example, the transformed cell expresses a recombinant form of a polypeptide or, in the case of anti-sense expression from the transferred gene, the expression of a naturally-occurring form of the protein is disrupted.

As used herein, the term "transgene" means a nucleic acid sequence encoding, e.g., one of the polypeptides, or an antisense transcript thereto, which is partly or entirely heterologous, i.e., foreign, to the transgenic animal or cell into which it is introduced, or, is homologous to an endogenous gene of the transgenic animal or cell into which it is introduced, but which is designed to be inserted, or is inserted, into the animal's genome in such a way as to alter the genome of the cell into which it is inserted (e.g., it is inserted at a location which differs from that of the natural gene or its insertion results in a knockout). A transgene can include one or more transcriptional regulatory sequences and any other nucleic acid, (e.g. as intron), that may be necessary for optimal expression of a selected nucleic acid.

A "transgenic animal" refers to any animal, preferably a non-human mammal, bird or an amphibian, in which one or more of the cells of the animal contain heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. The term genetic manipulation does not include classical cross-breeding, or in vitro fertilization, but rather is directed to the introduction of a recombinant DNA molecule. This molecule may be integrated within a chromosome, or it may be extrachromosomally replicating DNA. In the typical transgenic animals described herein, the transgene causes cells to express a recombinant form of one of the proteins, e.g. either agonistic or antagonistic forms. However, transgenic animals in which the recombinant gene is silent are also contemplated, as for example, the FLP or CRE recombinase dependent constructs described below. Moreover, "transgenic animal" also includes those recombinant animals in which gene disruption of one or more genes is caused by human intervention, including both recombination and antisense techniques.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/expression of nucleic acids to which they are linked. Vectors capable of directing the expression of genes to which they are operatively linked are referred to herein as "expression vectors". In general, expression vectors of utility in recombinant DNA techniques are often in the form of "plasmids" which refer generally to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The term "treating" as used herein is intended to encompass curing as well as ameliorating at least one symptom of a condition or disease.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

4.2 General

The instant invention is based on linkage studies that have mapped a macular degeneration causing gene to a region of human chromosome 2 and on sequencing studies that have identified mutations in the FBNL gene within the mapped region. As described in detail in the attached Example 1, linkage has been determined based on studies performed on eighty-six members of four families affected with radial drusen. One family was of American origin, while the other three originated in the Leventine valley of Switzerland. The pedigrees of these families are shown in FIG. 1.

As reported in the following Example 1, the gene responsible for macular degeneration maps on the short arm of chromosome 2. When mutated, the gene is capable of causing the development of autosomal dominant radial drusen (malattia leventinese or Doyne's honeycomb retinal dystrophy). All four families investigated have very similar clinical features and all four have positive lod scores (with no recombinants) with the most tightly linked markers.

Multipoint analysis revealed apeak lod score of 12 centered on marker GATA26H10. The lod-1 confidence interval was 8 cM40. The more conservative estimate of the diseased interval (defined by observed recombinations) is 14 cM extending from marker D2S1761 (centromeric) to D2S444 telomeric.

The interval has been haplotypically narrowed by analysis of the twenty Swiss Malattia Leventinese families. The haplotypic interval is defmed by markers D2S2352-D2S1364 (approximately 1 cM). The American Malattia Leventinese families also share haplotypic identity with the Swiss families from markers CA-133 to D2S1364<1 cM.

Genes that fall in the haplotypically identical Swiss interval are set forth in the following Table 1:

TABLE 1

| Marker | Gen Bank Accession Number | Expression (from Unigene) | Description |
| --- | --- | --- | --- |
| SGC35022 | H72600 | fetal liver/spleen | dual specificity protein kinase |
| WI-11560 | R08151 | fetal liver/spleen | |
| SGC32447 | RO9316 | brain | |
| SGC34889 | M66771 | fetal liver/spleen | |
| WI-6704 | Z38691 | infant brain, fetal heart | |
| WI6613 | | embryo retina, infant brain, fetal liver/spleen | |
| WI12526 | | | similar to spectrin B-g chain |
| B-fodrin | | brain | |
| WI-11791 | R28010 | placenta, fetal liver/spleen, melanocytes | |
| WI-11399 | T87762 | fetal liver/spleen | |

(Physical and genetic mapping for each marker information can be obtained from the Whitehead Institute for Genome Research (http://www-genome.wi.mit.edu).)

As described in Example 2, a genetic interval containing the mutated gene was developed by linkage and haplotype analysis of 36 nuclear families with MD from the US, Switzerland and Australia. A list of candidate genes was developed. A sequence variation was detected in a candidate gene (FBNL) that altered an amino acid in a non-conservative way. Specifically, this change alter the first nucleotide of codon 345 from a C to a T thereby changing the predicted amino acid at this position from an arginine to a tryptophan. Since different transcription start sites are possible for this gene, for clarity, the involved nucleotide is specified as being nucleotide 952 in the cDNA sequence posted as GenBank accession no. UO3877 (Seq. Id. No. 1). All 36 ML families (111 157 affected patients)share the same sequence variation. None of the 494 AMD patients (from the US, Australia and Switzerland and the US) exhibit this change. In addition, as described in Example 3, the sequence of a Swiss patient was found to contain a different amino acid change in exon 10:362 Arg>Gln.

It is not surprising that mutations in the FBNL gene have been identified as causing MD. This gene encodes an extracellular matrix protein which is the single most likely class of molecule to cause the accumulation of lipofuscin under the retinal pigment epithelium known as drusen (the hallmark of MD). In addition, its location is within the genetically defined disease interval. Thirdly, it has been found to be upregulated in patients with a genetic form of premature ageing (Werner' syndrome).

The finding that mutations in FBNL cause macular degeneration, makes macular degeneration testing a reality. Diagnostic testing can now be performed on presymptomatic individuals, who are at risk of developing macular degeneration based on family history. In addition, tests can be performed on postsymptomatic individuals diagnosed with macular degeneration based on an ophthalmologic examination.

In addition to being used diagnostically, identification of the involvement of mutations in the FBNL gene in the development of macular degenerations allows the production of cell-free and cell-based screening assays and transgenic animals for use in further studies of the disorder and to identify safe and effective MD therapeutics.

The identification of a single gene known to be responsible for AMD can also improve understanding of the types and classes of genes that can cause related disorders. In addition, the identification of one gene product causing a disorder can make it possible to identify other genes which can cause a similar phenotype. For example, the identification of the dystrophin gene has led to the isolation of dystrophin related glycoproteins, at least one of which plays a role in other forms of muscular dystrophy. Also, a gene capable of causing a Mendelian disorder, may contribute to the inheritance of a multifactorial form of the disorder. A striking example of this has been the identification of genes involved in various forms of cancer (e.g. colon cancer) by studying familial forms of cancer (e.g. hereditary nonpolyposis colon cancer and familial adenomatous polyposis). Groden, J. A. et al.,(1991) *Cell* 66:589–600 ; Aaltonen, L. A. (1993) *Science* 260:812–816). For example, as shown herein, AMD appears to be allelic to Doyne's macular dystrophy.

4.3 Predictive Medicine
4.3. MD Causative Mutations

The invention is based, at least in part, on the identification of mutations that cause Macular Degeneration (MD). Because the particular MD mutations may be in linkage disequilibrium with other alleles, the detection of such other alleles can also indicate a predisposition to developing MD in a subject.

4.3. Detection of Alleles

Many methods are available for detecting specific alleles at human polymorphic loci. The preferred method for detecting a specific polymorphic allele may depend, in part, upon the molecular nature of the polymorphism. For example, detection of specific alleles may be nucleic acid techniques based on hybridization, size, or sequence, such as restriction fragment length polymorphism (RFLP), nucleic acid sequencing, and allele specific oligonucleotide (ASO) hybridization. In one embodiment, the methods comprise detecting in a sample of DNA obtained from a subject the existence of an allele associated with MD. For example, a nucleic acid composition comprising a nucleic acid probe including a region of nucleotide sequence which is capable of hybridizing to a sense or antisense sequence to an allele associated with MD can be used as follows: the nucleic acid in a sample is rendered accessible for hybridization, the probe is contacted with the nucleic acid of the sample, and the hybridization of the probe to the sample nucleic acid is detected. Such technique can be used to detect alterations or allelic variants at either the genomic or MRNA level as well as to determine MRNA transcript levels, when appropriate.

A preferred detection method is ASO hybridization using probes overlapping an allele associated with MD and has about 5, 10, 20, 25, or 30 nucleotides around the mutation or polymorphic region. In a preferred embodiment of the invention, several probes capable of hybridizing specifically to other allelic variants involved in MD are attached to a solid phase support, e.g., a "chip" (which can hold up to about 250,000 oligonucleotides). Oligonucleotides can be bound to a solid support by a variety of processes, including lithography. Mutation detection analysis using these chips comprising oligonucleotides, also termed "DNA probe arrays" is described e.g., in Cronin et al., *Human Mutation* 7:244, 1996. In one embodiment, a chip comprises all the allelic variants of at least one polymorphic region of a gene. The solid phase support is then contacted with a test nucleic acid and hybridization to the specific probes is detected. Accordingly, the identity of numerous allelic variants of one or more genes can be identified in a simple hybridization experiment.

These techniques may also comprise the step of amplifying the nucleic acid before analysis. Amplification techniques are known to those of skill in the art and include, but are not limited to cloning, polymerase chain reaction (PCR), polymerase chain reaction of specific alleles (ASA), ligase chain reaction (LCR), nested polymerase chain reaction, self sustained sequence replication (Guatelli, J. C. et al., *Proc. Natl. Acad. Sci. USA* 87:1874–78, 1990), transcriptional amplification system (Kwoh, D. Y. et al., *Proc. Natl. Acad. Sci. USA* 86:1173–77, 1989), and Q-Beta Replicase (Lizardi, P. M. et al., *Bio/Technology* 6:1197, 1988).

Amplification products may be assayed in a variety of ways, including size analysis, restriction digestion followed by size analysis, detecting specific tagged oligonucleotide primers in the reaction products, ASO hybridization, allele specific 5' exonuclease detection, sequencing, hybridization, and the like.

PCR based detection means can include multiplex amplification of a plurality of markers simultaneously. For example, it is well known in the art to select PCR primers to generate PCR products that do not overlap in size and can be analyzed simultaneously. Alternatively, it is possible to amplify different markers with primers that have detectable labels that are different and thus can each be differentially detected. Of course, hybridization based detection means allow the differential detection of multiple PCR products in a sample. Other techniques are known in the art to allow multiplex analyses of a plurality of markers.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize to an allele associated with MD, under conditions such that hybridization and amplification of the desired marker occurs, and (iv) detecting the amplification product. These detection schemes are especially useful for the detection of nucleic acid molecules if such molecules are present in very low numbers.

An allele associated with MD can also be identified by alterations in restriction enzyme cleavage patterns through RFLP analysis. For example, sample and control DNA is isolated, amplified (optionally), digested with one or more restriction endonucleases, and fragment length sizes are determined by gel electrophoresis through size fractionization.

In yet another embodiment, any of a variety of sequencing reactions known in the art can be used to directly sequence a polymorphic site having at least one allele associated with MD. Exemplary sequencing reactions include those based on techniques developed by Maxim and Gilbert (*Proc. Nati. Acad. Sci. USA* 74:560, 1977) or Sanger (Sanger et al., *Proc. Nat. Acad. Sci. USA* 74:5463, 1977). It is also contemplated that any of a variety of automated sequencing procedures may be utilized when performing the subject assays (*Biotechniques* 19:448, 1995), including sequencing by mass spectrometry (see, for example PCT publication WO 94/16101; Cohen et al, *Adv. Chromatogr.* 36:127–62, 1996; and Griffin et al., *Appl. Biochem. Biotechnol.* 38:147–59, 1993). It will be evident to one skilled in the art that, for certain embodiments, the occurrence of only one, two or three of the nucleic acid bases need be determined in the sequencing reaction. For instance, A-track or the like, e.g., where only one nucleic acid is detected, can be carried out.

In a further embodiment, protection from cleavage agents (such as a nuclease, hydroxylamine or osmium tetroxide and with piperidine) can be used to detect mismatched bases in RNA/RNA or RNA/DNA or DNA/DNA heteroduplexes (Myers et al., *Science* 230;1242, 1985). In general, the art technique of "mismatch cleavage" starts by providing heteroduplexes formed by hybridizing (labelled) RNA or DNA containing the wild-type allele with the sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with S1 nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. (See, for example, Cotton et al., *Proc. Natl. Acad. Sci. USA* 85:4397, 1988; Saleeba et al., *Methods Enzymol.* 217:286–95, 1992) In a preferred embodiment, the control DNA or RNA can have a detectable label.

In still another embodiment, the mismatch cleavage reaction employs one or more proteins that recognize mismatched base pairs in double-stranded DNA (so called "DNA mismatch repair" enzymes). For example, the mutY enzyme of *E. coli* cleaves A at G/A mismatches and the thymidine DNA glycosylase from HeLa cells cleaves T at G/T mismatches (Hsu et al., *Carcinogenesis* 15:1657–62, 1994). According to an exemplary embodiment, an appropriate probe is hybridized to a cDNA or other DNA product from a test cell(s). The duplex is treated with a DNA mismatch repair enzyme, and the cleavage products, if any, can be detected from electrophoresis protocols or the like. (See, for example, U.S. Pat. No. 5,459,039.)

In other embodiments, alterations in electrophoretic mobility will be used to identify an allele associated with MD. For example, single strand conformation polymorphism (SSCP) may be used to detect differences in electrophoretic mobility between mutant and wild type nucleic acids (Orita et al., *Proc. Natl. Acad. Sci. USA* 86:2766, 1989, see also Cotton, *Mutat. Res.* 285:125–44, 1993; and Hayashi, *Genet. Anal. Tech. Appl.* 9:73–79, 1992. Single-stranded DNA fragments of sample and control are denatured and allowed to renature. The secondary structure of single-stranded nucleic acids varies according to sequence, the resulting alteration in electrophoretic mobility enables the detection of even a single base change. The DNA fragments may be labeled or detected with labeled probes, such as primers with a detectable label. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al., *Trends Genet.* 7:5, 1991).

In yet another embodiment, the movement of an allele associated with MD in polyacrylamide gels containing a gradient of denaturant is assayed using denaturing gradient gel electrophoresis (DGGE) (Myers et al., *Nature* 313:495, 1985). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing agent gradient to identify differences in the mobility of control and sample DNA (Rosenbaum and Reissner, *Biophys. Chem.* 265:12753, 1987).

Examples of other techniques for detecting alleles associated with MD include, but are not limited to, selective oligonucleotide hybridization, selective amplification, or selective primer extension. For example, oligonucleotide primers may be prepared in which the known mutation or nucleotide difference (e.g., in allelic variants) is placed centrally and then hybridized to target DNA under conditions which permit hybridization only if a perfect match is found (Saiki et al., *Nature* 324:163, 1986); Saiki et al., *Proc. Natl. Acad. Sci. USA* 86:6230, 1989). Such ASO hybridization techniques may be used to test one mutation or polymorphic region per reaction when oligonucleotides are hybridized to PCR amplified target DNA or a number of different mutations or polymorphic regions when the oligonucleotides are attached to the hybridizing membrane and hybridized with labelled target DNA.

Alternatively, allele specific amplification technology which depends on selective PCR amplification may be used in conjunction with the instant invention. Oligonucleotides used as primers for specific amplification may carry the mutation or polymorphic region of interest in the center of the molecule (so that amplification depends on differential hybridization) (Gibbs et al., *Nucleic Acids Res.* 17:2437–2448, 1989) or at the extreme 3' end of one primer where, under appropriate conditions, mismatch can prevent, or reduce polymerase extension (Prossner, *Tibtech* 11:238, 1993. In addition it may be desirable to introduce a novel restriction site in the region of the mutation to create cleavage-based detection (Gasparini et al., *Mol. Cell Probes* 6:1, 1992). It is anticipated that in certain embodiments amplification may also be performed using Taq ligase for amplification (Barany, *Proc. Natl. Acad. Sci USA* 88:189, 1991). In such cases, ligation will occur only if there is a perfect match at the 3' end of the 5' sequence making it possible to detect the presence of a known mutation at a specific site by looking for the presence or absence of amplification.

In another embodiment, identification of the allelic variant is carried out using an oligonucleotide ligation assay (OLA), as described, e.g., in U.S. Pat. No. 4,998,617 and in Landegren et al., *Science* 241:1077–80, 1988. The OLA protocol uses two oligonucleotides which are designed to be capable of hybridizing to abutting sequences of a single strand of a target. One of the oligonucleotides is linked to a separation marker, e.g,. biotinylated, and the other has a detectable label. If the precise complementary sequence is found in a target molecule, the oligonucleotides will hybridize such that their termini abut, and create a ligation substrate. Ligation then permits the labeled oligonucleotide to be recovered using avidin, or another biotin ligand. Nickerson, D. A. et al. have described a nucleic acid detection assay that combines attributes of PCR and OLA (Nickerson et al., *Proc. Natl. Acad. Sci.* USA 87:8923–27, 1990. In this method, PCR is used to achieve the exponential amplification of target DNA, which is then detected using OLA.

Several techniques based on this OLA method have been developed and can be used to detect alleles associated with MD. For example, U.S. Pat. No. 5,593,826 discloses an OLA using an oligonucleotide having 3'-amino group and a 5'-phosphorylated oligonucleotide to form a conjugate having a phosphoramidate linkage. In another variation of OLA described in Tobe et al., *Nucleic Acids Res.* 24:3728, 1996, OLA combined with PCR permits typing of two alleles in a single microtiter well. By marking each of the allele-specific primers with a unique hapten, i.e. digoxigenin and fluorescein, each OLA reaction can be detected by using hapten specific antibodies that are labeled with different enzyme reporters, alkaline phosphatase or horseradish peroxidase. This system permits the detection of the two alleles using a high throughput format that leads to the production of two different colors.

Several methods have been developed to facilitate analysis of single nucleotide polymorphisms. In one embodiment, the single base polymorphism can be detected by using a specialized exonuclease-resistant nucleotide, as disclosed, e.g., in U.S. Pat. No. 4,656,127 (Mundy et al.). According to the method, a primer complementary to the allelic sequence immediately 3' to the polymorphic site is permitted to hybridize to a target molecule obtained from a particular animal or human. If the polymorphic site on the target molecule contains a nucleotide that is complementary to the particular exonuclease-resistant nucleotide derivative present, then that derivative will be incorporated onto the end of the hybridized primer. Such incorporation renders the primer resistant to exonuclease, and thereby permits its detection. Since the identity of the exonuclease-resistant derivative of the sample is known, a fmding that the primer has become resistant to exonucleases reveals that the nucleotide present in the polymorphic site of the target molecule was complementary to that of the nucleotide derivative used in the reaction. This method has the advantage that it does not require the determination of large amounts of extraneous sequence data.

In another embodiment of the invention, a solution-based method is used for determining the identity of the nucleotide of a polymorphic site. French Patent 2,650,840; PCT Appln. No. WO91/02087. As in the Mundy method of U.S. Pat. No. 4,656,127, a primer is employed that is complementary to allelic sequences immediately 3' to a polymorphic site. The method determines the identity of the nucleotide of that site using labeled dideoxynucleotide derivatives, which, if complementary to the nucleotide of the polymorphic site will become incorporated onto the terminus of the primer.

An alternative method, known as Genetic Bit Analysis or GBA ™ is described by Goelet et al. in PCT Appln. No. 92/15712. The method of Goelet et al. uses mixtures of labeled terminators and a primer that is complementary to the sequence 3' to a polymorphic site. The labeled terminator that is incorporated is thus determined by, and complementary to, the nucleotide present in the polymorphic site of the target molecule being evaluated. In contrast to the method of Cohen et al., French Patent 2,650,840 and PCT Appln. No. WO91/02087, the method of Goelet et al. is preferably a heterogeneous phase assay, in which the primer or the target molecule is immobilized to a solid phase.

Recently, several primer-guided nucleotide incorporation procedures for assaying polymorphic sites in DNA have been described (Komher et al., Nucleic Acids Res. 17:7779–84, 1989; Sokolov, *Nucleic Acids Res.* 18:3671, 1990; Syvanen et al., *Genomics* 8:684–92, 1990; Kuppuswamy et al., *Proc. Natl. Acad. Sci. USA* 88:1143–47, 1991; Prezant et al., *Hum. Mutat.* 1:159–64, 1992; Ugozzoli et al., GATA 9:107–12, 1992; Nyren et al., *Anal. Biochem.* 208:171–75, 1993). These methods differ from GBA ™ in that they all rely on the incorporation of labeled deoxynucleotides to discriminate between bases at a polymorphic site. In such a format, since the signal is proportional to the number of deoxynucleotides incorporated, polymorphisms that occur in runs of the same nucleotide can result in signals that are proportional to the length of the run (Syvanen, et al., *Amer. J Hum. Genet.* 52:46–59, 1993).

For mutations that produce premature termination of protein translation, the protein truncation test (PTT) offers an efficient diagnostic approach (Roest. et. al., *Hum. Mol. Genet.* 2:1719–21, 1993; van der Luijt et. al., *Genomics* 20:1–4, 1994). For PTT, RNA is initially isolated from available tissue and reverse-ranscribed, and the segment of interest is amplified by PCR. The products of reverse transcription PCR are then used as a template for nested PCR amplification with a primer that contains an RNA polymerase promoter and a sequence for initiating eukaryotic translation. After amplification of the region of interest, the unique motifs incorporated into the primer permit sequential in vitro transcription and translation of the PCR products. Upon sodium dodecyl sulfate-polyacrylamide gel electrophoresis of translation products, the appearance of truncated polypeptides signals the presence of a mutation that causes premature termination of translation. In a variation of this technique, DNA (as opposed to RNA) is used as a PCR template when the target region of interest is derived from a single exon.

In still another method known as Dynamic Allele Specific Hybridization (DASH), a target sequence is amplified by PCR in which one primer is biotinylated. The biotinylated product strand is bound to a streptavidin or avidin coated microtiter plate well, and the non-biotinylated strand is rinsed away with alkali. An oligonucleotide probe, specific for one allele, is hybridized to the target at low temperature. This forms a duplex DNA region that interacts with a double strand-specific intercalating dye. Upon excitation, the dye emits fluorescence proportional to the amount of double stranded DNA (probe-target duplex) present. The sample is then steadily heated while fluorescence is continually monitored. A rapid fall in fluorescence indicates the denaturing (or "melting") temperature of the probe-target duplex. When performed under appropriate buffer and dye conditions, a single-base mismatch between the probe and the target results in a dramatic lowering of melting temperature (Tm) that can be easily detected (Howell, W. M. et al., (1999) Nature *Biotechnology* 1 7:)87–88.

Any cell type or tissue may be utilized in the diagnostics described herein. In a preferred embodiment the DNA sample is obtained from a bodily fluid obtained by known techniques. Alternatively, nucleic acid tests can be performed on dry samples (e.g. hair or skin).

Diagnostic procedures may also be performed in situ directly upon tissue sections (fixed and/or frozen) of patient tissue obtained from biopsies or resections, such that no nucleic acid purification is necessary. Nucleic acid reagents may be used as probes and/or primers for such in situ procedures (see, for example, Nuovo, PCR in situ Hybridization: Protocols and Applications (Raven Press, N.Y., 1992)).

In addition to methods which focus primarily on the detection of one nucleic acid sequence, profiles may also be assessed in such detection schemes. Fingerprint profiles may be generated, for example, by utilizing a differential display procedure, Northern analysis and/or RT-PCR.

Another embodiment of the invention is directed to kits. This kit may contain one or more oligonucleotides, including 5' and 3' oligonucleotides that hybridize 5' and 3' to a polymorphic site having as allele associated with MD or detection oligonucleotides that hybridize directly to an allele associate with MD. The kit may also contain one or more oligonucleotides capable of hybridizing near or at other alleles that are in linkage disequilibrium with an MD causing allele (mutation). PCR amplification oligonucleotides should hybridize between 25 and 2500 base pairs apart, preferably between about 100 and about 500 bases apart, in order to produce a PCR product of convenient size for subsequent analysis.

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ oligonucleotides having detectable labels to allow ease of identification in the assays. Examples of labels which may be employed include radio-labels, enzymes, fluorescent compounds, streptavidin, avidin, biotin, magnetic moieties, metal binding moieties, antigen or antibody moieties, and the like. Oligonucleotides useful in kits as well as other aspects of the present invention are selected from the group consisting of any oligonucleotides that overlap or are contained in SEQ. ID. Nos. 3 and 4.

One of skill in the art can readily determine additional useful oligonucleotide sequences based on the sequences provided herein.

The kit may, optionally, also include DNA sampling means; DNA purification reagents such as Nucleon™ kits, lysis buffers, proteinase solutions and the like; PCR reagents, such as 10× reaction buffers, thermostable polymerase, dNTPs, and the like; and DNA detection means such as appropriate restriction enzymes, allele specific oligonucleotides, degenerate oligonucleotide primers for nested PCR.

4.3. Pharmacogenomics,

Knowledge of the particular MD associated mutations, alone or in conjunction with information on other genetic defects contributing to MD (the genetic profile of MD) allows a customization of the therapy to the individual's genetic profile, the goal of "pharmacogenomics". Thus, comparison of a subject's particular genetic profile to the genetic profile of MD, permits the selection or design of drugs that are expected to be safe and efficacious for a particular patient or patient population (i.e., a group of patients having the same genetic alteration).

The ability to target populations expected to show the highest clinical benefit, based on genetic profile, can enable: 1) the repositioning of marketed drugs with disappointing market results; 2) the rescue of drug candidates whose clinical development has been discontinued as a result of safety or efficacy limitations, which are patient subgroup-specific; and 3) an accelerated and less costly development for drug candidates and more optimal drug labeling (e.g. since measuring the effect of various doses of an agent on an MD causative mutation is useful for optimizing effective dose).

Cells of a subject may also be obtained before and after administration of a candidate MD therapeutic to detect the level of expression of genes other than FBNL, to verify that the therapeutic does not increase or decrease the expression of genes which could be deleterious. This can be done, e.g., by using the method of transcriptional profiling. Thus, mRNA from cells exposed in vivo to a therapeutic and mRNA from the same type of cells that were not exposed to the therapeutic could be reverse transcribed and hybridized to a chip containing DNA from numerous genes, to thereby compare the expression of genes in cells treated and not treated with the therapeutic.

4.4. MD Therapeutics 4.4.1 MD Therapeutics

Agents that are useful in treating or preventing the development of a Macular Degeneration can comprise nucleic acids (e.g. genes, fragments thereof, antisense molecule, proteins (e.g. glycosylated or unglycosylated protein, polypeptide or protein) or other organic or inorganic molecules (e.g. small molecules) that interfere with or compensate for the biochemical events that are causative of MD. The following describes in vitro and in vivo assays for identifying and/or testing candidate MD therapeutics.

4.4.2. Cell Based and Cell Free Assays for Identifying MD Therapeutics

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity and/or bioavailability of the test compound can be generally ignored in the in vitro system, the assay instead being focused primarily on the effect of the drug on the molecular target as may be manifest in an alteration of binding affinity with upstream or downstream elements.

Accordingly, in an exemplary screening assay of the present invention, the compound of interest is contacted with a protein which may function upstream (including both activators (enhancers) and repressors of its activity) or to proteins and/or nucleic acids (e.g. promoter) which may function downstream of the FBNL polypeptide, whether they are positively or negatively regulated by it. To the mixture of the compound and the upstream or downstream element is then added a composition containing an FBNL polypeptide. Detection and quantification of complexes of FBNL with it's upstream or downstream elements provide a means for determining a compound's efficacy at antagonizing (inhibiting) or agonizing (potentiating) complex formation between an FBNL protein and an FBNL binding element (e.g. protein or nucleic acid). The efficacy of the compound can be assessed by generating dose response curves from data obtained using various concentrations of the test compound. Moreover, a control assay can also be performed to provide a baseline for comparison. In the control assay, isolated and purified FBNL polypeptide is added to a composition containing the FBNL binding element, and the formation of a complex is quantitated in the absence of the test compound.

Complex formation between the FBNL polypeptide and a binding element may be detected by a variety of techniques. Modulation of the formation of complexes can be quantitated using, for example, detectably labeled proteins such as radiolabeled, fluorescently labeled, or enzymatically labeled FBNL polypeptides, by immunoassay, or by chromatographic detection.

Typically, it will be desirable to immobilize either FBNL protein or its binding protein to facilitate separation of complexes from uncomplexed forms of one or both of the proteins, as well as to accommodate automation of the assay. Binding of FBNL to an upstream or downstream element, in the presence or absence of a candidate agent, can be accomplished in any vessel suitable for containing the reactants. Examples include microtitre plates, test tubes, and microcentrifuge tubes. In one embodiment, a fusion protein can be provided which adds a domain that allows the protein to be bound to a matrix. For example, glutathione-S-transferase/FBNL (GST/FBNL) fusion proteins can be adsorbed onto glutathione sepharose beads (Sigma Chemical, St. Louis, Mo.) or glutathione derivatized microtitre plates, which are then combined with the cell lysates, e.g. an $^{35}$S-labeled, and the test compound, and the mixture incubated under conditions conducive to complex formation, e.g. at physiological conditions for salt and pH, though slightly more stringent conditions may be desired. Following incubation, the beads are washed to remove any unbound label, and the matrix immobilized and radiolabel determined directly (e.g. beads placed in scintillant), or in the supernatant after the complexes are subsequently dissociated. Alternatively, the complexes can be dissociated from the matrix, separated by SDS-PAGE, and the level of FBNL-binding protein found in the bead fraction quantitated from the gel using standard electrophoretic techniques.

Other techniques for immobilizing proteins on matrices are also available for use in the subject assay. For instance, an FBNL protein or its cognate binding protein can be immobilized utilizing conjugation of biotin and streptavidin. For instance, biotinylated molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96 well plates (Pierce Chemical). Alternatively, antibodies reactive with FBNL or with a protein encoded by a gene that is up- or down- regulated by FBNL can be derivatized to the wells of the plate, and protein trapped in the wells by antibody conjugation. As above, preparations of a binding protein and a test compound are incubated in the protein presenting wells of the plate, and the amount of complex trapped in the well can be quantitated. Exemplary methods for detecting such complexes, in addition to those described above for the GST-immobilized complexes, include immunodetection of complexes using antibodies reactive with the protein binding element, or which are reactive with the FBNL protein; as well as enzyme-linked assays which rely on detecting an enzymatic activity associated with the binding element, either intrinsic or extrinsic activity. In the instance of the latter, the enzyme can be chemically conjugated or provided as a fusion protein with the binding partner. To illustrate, the binding partner can be chemically cross-linked or genetically fused with horseradish peroxidase, and the amount of polypeptide trapped in the complex can be assessed with a chromogenic substrate of the enzyme, e.g. 3,3'-diamino-benzadine terahydrochloride or 4-chloro-1-napthol. Likewise, a fusion protein comprising the polypeptide and glutathione-S-transferase can be provided, and complex formation quantitated by detecting the GST activity using 1-chloro-2,4-dinitrobenzene (Habig et al. (1974) *J Biol Chem* 249:7130).

For processes which rely on immunodetection for quantitating one of the proteins trapped in the complex, antibodies against the protein can be used. Alternatively, the protein to be detected in the complex can be "epitope tagged" in the form of a fusion protein which includes, in addition to the FBNL sequence, a second polypeptide for which antibodies are readily available (e.g. from commercial sources). For instance, the GST fusion proteins described above can also be used for quantification of binding using antibodies against the GST moiety. Other useful epitope tags include myc-epitopes (e.g., see Ellison et al. (1991) *J Biol Chem* 266:21150–21157) which includes a 10-residue sequence from c-myc, as well as the pFLAG system (International Biotechnologies, Inc.) or the pEZZ-protein A system (Pharamacia, N.J.). Transcription factor-DNA binding assays are described in U.S. Pat. No. 5,563,036, which is owned by Tularik and is specifically incorporated by reference herein.

Further, an in vitro assays can be used to detect compounds which can be used for treatment of MD. For example, cells can be engineered to express an FBNL gene (wildtype or mutant) in operative linkage with a reporter gene construct, such as luciferase or chloramphenicol acetyl transferase, or other reporter gene known in the art. Cells can then be contacted with test compounds and the rate or level of FBNL expression can be assayed to identify agonists or antagonists.

Also, a DNA footprinting assay can be used to detect compounds which alter the binding of an FBNL protein to nucleic acids (see for example, Zhong et al. 1994 *Mol. Cell Biol.* 14:7276). Further, FBNL may be transitionally or post-transitionally modified by processes such as mRNA editing or protein truncation. Assays to specifically monitor these processes can be performed according to protocols, which are well-known in the art.

In addition to cell-free assays, such as described above, the FBNL proteins provided by the present invention also facilitates the generation of cell-based assays for identifying small molecule agonists/antagonists and the like. For example, cells can be caused to overexpress a recombinant FBNL protein in the presence and absence of a test agent of interest, with the assay scoring for modulation in FBNL responses by the target cell mediated by the test agent. As with the cell-free assays, agents which produce a statistically significant change in FBNL-dependent responses (either inhibition or potentiation) can be identified.

Exemplary cell lines may include retinal pigment epithelial cell lines. Further, the transgenic animals discussed herein may be used to generate cell lines, containing one or more cell types involved in MD, that can be used as cell culture models for this disorder. While primary cultures may be utilized, the generation of continuous cell lines is preferred. For examples of techniques which may be used to derive a continuous cell line from the transgenic animals, see Small et al., 1985, *Mol. Cell Biol.* 5:642–648.

For example, the effect of a test compound on a variety of end points could be tested. Similarly, epithelial cells can be treated with test compounds or transfected with genetically engineered FBNL genes. Monitoring the influence of compounds on cells may be applied not only in basic drug screening, but also in clinical trials. In such clinical trials, the expression of a panel of genes may be used as a "read out" of a particular drug's therapeutic effect.

In yet another aspect of the invention, the subject FBNL polypeptides can be used in a "two hybrid" assay (see, for example, U.S. Pat. No. 5,283,317; Zervos et al. (1993) *Cell* 72:223–232; Madura et al. (1993) *J Biol Chem* 268:12046–12054; Bartel et al. (1993) *Biotechniques* 14:920–924; Iwabuchi et al. (1993) *Oncogene* 8:1693–1696; and Brent WO94/10300), for isolating coding sequences for other cellular proteins which bind to or interact with an FBNL(e.g., FBNL binding proteins" or "FBNLbp").

Briefly, the two hybrid assay relies on reconstituting in vivo a functional transcriptional activator protein from two separate fusion proteins. In particular, the method makes use of chimeric genes which express hybrid proteins. To illustrate, a first hybrid gene comprises the coding sequence for a DNA-binding domain of a transcriptional activator fused in frame to the coding sequence for an FBNL polypeptide. The second hybrid protein encodes a transcriptional activation domain fused in frame to a sample gene from a cDNA library. If the bait and sample hybrid proteins are able to interact, e.g., form an FBNL dependent complex, they bring into close proximity the two domains of the transcriptional activator. This proximity is sufficient to cause transcription of a reporter gene which is operably linked to a transcriptional regulatory site responsive to the transcriptional activator, and expression of the reporter gene can be detected and used to score for the interaction of the FBNL and sample proteins.

4.4.3 Transgenic Animals For Identifying MD Therapeutics

Transgenic animals can also be made to identify MD therapeutics, to confirm the safety and efficacy of a candidate therapeutic or to study drusen formation. Transgenic animals of the invention can include non-human animals containing an MD causative mutation under the control of an appropriate homologous or heterologous promoter.

Methods for obtaining transgenic non-human animals are well known in the art. In preferred embodiments, the expression of an MD causative mutation is restricted to specific subsets of cells, tissues or developmental stages utilizing, for example, cis-acting sequences that control expression in the desired pattern. In the present invention, such mosaic expression can be essential for many forms of lineage analysis and can additionally provide a means to assess the effects of, for example, expression level which might grossly alter development in small patches of tissue within an otherwise normal embryo. Toward this end, tissue-specific regulatory sequences and conditional regulatory sequences can be used to control expression of the mutation in certain spatial patterns. Moreover, temporal patterns of expression can be provided by, for example, conditional recombination systems or prokaryotic transcriptional regulatory sequences. Genetic techniques, which allow for the expression of the mutation can be regulated via site-specific genetic manipulation in vivo, are known to those skilled in the art.

The transgenic animals of the present invention all include within a plurality of their cells an MD causative mutation transgene of the present invention, which transgene alters the phenotype of the "host cell". In an illustrative embodiment, either the cre/loxP recombinase system of bacteriophage P1 (Lakso et al. (1992) PNAS 89:6232–6236; Orban et al. (1992) PNAS 89:6861–6865) or the FLP recombinase system of *Saccharomyces cerevisiae* (O'Gorman et al. (1991) *Science* 251:1351–1355; PCT publication WO 92/15694) can be used to generate in vivo site-specific genetic recombination systems. Cre recombinase catalyzes the site-specific recombination of an intervening target sequence located between loxP sequences. loxP sequences are 34 base pair nucleotide repeat sequences to which the Cre recombinase binds and are required for Cre recombinase mediated genetic recombination. The orientation of loxP sequences determines whether the intervening target sequence is excised or inverted when Cre recombinase is present (Abremski et al. (1984) *J Biol. Chem.* 259:1509–1514); catalyzing the excision of the target sequence when the loxP sequences are oriented as direct repeats and catalyzes inversion of the target sequence when loxP sequences are oriented as inverted repeats.

Accordingly, genetic recombination of the target sequence is dependent on expression of the Cre recombinase. Expression of the recombinase can be regulated by promoter elements which are subject to regulatory control, e.g., tissue-specific, developmental stage-specific, inducible or repressible by externally added agents. This regulated control will result in genetic recombination of the target sequence only in cells where recombinase expression is mediated by the promoter element. Thus, the activation of expression of a mutation containing transgene can be regulated via control of recombinase expression.

Use of the cre/loxP recombinase system to regulate expression of a mutation containing transgene requires the construction of a transgenic animal containing transgenes encoding both the Cre recombinase and the subject protein. Animals containing both the Cre recombinase and the mutation transgene can be provided through the construction of "double" transgenic animals. A convenient method for providing such animals is to mate two transgenic animals each containing a transgene.

Similar conditional transgenes can be provided using prokaryotic promoter sequences which require prokaryotic proteins to be simultaneously expressed in order to facilitate expression of the transgene. Exemplary promoters and the corresponding trans-activating prokaryotic proteins are given in U.S. Pat. No. 4,833,080.

Moreover, expression of the conditional transgenes can be induced by gene therapy-like methods wherein a gene encoding the transactivating protein, e.g. a recombinase or a prokaryotic protein, is delivered to the tissue and caused to be expressed, such as in a cell-type specific manner. By this method, the transgene could remain silent into adulthood until "turned on" by the introduction of the transactivator.

In an exemplary embodiment, the "transgenic non-human animals" of the invention are produced by introducing transgenes into the germline of the non-human animal. Embryonal target cells at various developmental stages can be used to introduce transgenes. Different methods are used depending on the stage of development of the embryonal target cell. The specific line(s) of any animal used to practice this invention are selected for general good health, good embryo yields, good pronuclear visibility in the embryo, and good reproductive fitness. In addition, the haplotype is a significant factor. For example, when transgenic mice are to be produced, strains such as C57BL/6 or FVB lines are often used (Jackson Laboratory, Bar Harbor, Me.). Preferred strains are those with $H-2^b$, $H-2^d$ or $H-2^q$ haplotypes such as C57BL/6 or DBA/1. The line(s) used to practice this invention may themselves be transgenics, and/or may be knockouts (i.e., obtained from animals which have one or more genes partially or completely suppressed). In one embodiment, the transgene construct is introduced into a single stage embryo. The zygote is the best target for microinjection. In the mouse, the male pronucleus reaches the size of approximately 20 micrometers in diameter which allows reproducible injection of 1–2 pl of DNA solution. The use of zygotes as a target for gene transfer has a major advantage in that in most cases the injected DNA will be incorporated into the host gene before the first cleavage (Brinster et al. (1985) *PNAS* 82:4438–4442). As a consequence, all cells of the transgenic animal will carry the incorporated transgene. This will in general also be reflected in the efficient transmission of the transgene to offspring of the founder since 50% of the germ cells will harbor the transgene.

Normally, fertilized embryos are incubated in suitable media until the pronuclei appear. At about this time, the nucleotide sequence comprising the transgene is introduced into the female or male pronucleus as described below. In some species such as mice, the male pronucleus is preferred. It is most preferred that the exogenous genetic material be added to the male DNA complement of the zygote prior to its being processed by the ovum nucleus or the zygote female pronucleus. It is thought that the ovum nucleus or female pronucleus release molecules which affect the male DNA complement, perhaps by replacing the protamines of the male DNA with histones, thereby facilitating the combination of the female and male DNA complements to form the diploid zygote.

Thus, it is preferred that the exogenous genetic material be added to the male complement of DNA or any other complement of DNA prior to its being affected by the female pronucleus. For example, the exogenous genetic material is added to the early male pronucleus, as soon as possible after the formation of the male pronucleus, which is when the male and female pronuclei are well separated and both are located close to the cell membrane. Alternatively, the exogenous genetic material could be added to the nucleus of the sperm after it has been induced to undergo decondensation. Sperm containing the exogenous genetic material can then be added to the ovum or the decondensed sperm could be added to the ovum with the transgene constructs being added as soon as possible thereafter.

Introduction of the transgene nucleotide sequence into the embryo may be accomplished by any means known in the art such as, for example, microinjection, electroporation, or lipofection. Following introduction of the transgene nucleotide sequence into the embryo, the embryo may be incubated in vitro for varying amounts of time, or reimplanted into the surrogate host, or both. In vitro incubation to maturity is within the scope of this invention. One common method in to incubate the embryos in vitro for about 1–7 days, depending on the species, and then reimplant them into the surrogate host.

For the purposes of this invention a zygote is essentially the formation of a diploid cell which is capable of developing into a complete organism. Generally, the zygote will be comprised of an egg containing a nucleus formed, either naturally or artificially, by the fusion of two haploid nuclei from a gamete or gametes. Thus, the gamete nuclei must be ones which are naturally compatible, i.e., ones which result in a viable zygote capable of undergoing differentiation and developing into a functioning organism. Generally, a euploid zygote is preferred. If an aneuploid zygote is obtained, then the number of chromosomes should not vary by more than one with respect to the euploid number of the organism from which either gamete originated.

In addition to similar biological considerations, physical ones also govern the amount (e.g., volume) of exogenous genetic material which can be added to the nucleus of the zygote or to the genetic material which forms a part of the zygote nucleus. If no genetic material is removed, then the amount of exogenous genetic material which can be added is limited by the amount which will be absorbed without being physically disruptive. Generally, the volume of exogenous genetic material inserted will not exceed about 10 picoliters. The physical effects of addition must not be so great as to physically destroy the viability of the zygote. The biological limit of the number and variety of DNA sequences will vary depending upon the particular zygote and functions of the exogenous genetic material and will be readily apparent to one skilled in the art, because the genetic material, including the exogenous genetic material, of the resulting zygote must be biologically capable of initiating and maintaining the differentiation and development of the zygote into a functional organism.

The number of copies of the transgene constructs which are added to the zygote is dependent upon the total amount of exogenous genetic material added and will be the amount which enables the genetic transformation to occur. Theoretically only one copy is required; however, generally, numerous copies are utilized, for example, 1,000–20,000 copies of the transgene construct, in order to insure that one copy is functional. As regards the present invention, there will often be an advantage to having more than one functioning copy of each of the inserted exogenous DNA sequences to enhance the phenotypic expression of the exogenous DNA sequences.

Any technique which allows for the addition of the exogenous genetic material into nucleic genetic material can be utilized so long as it is not destructive to the cell, nuclear membrane or other existing cellular or genetic structures. The exogenous genetic material is preferentially inserted into the nucleic genetic material by microinjection. Microinjection of cells and cellular structures is known and is used in the art.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Transgenic offspring of the surrogate host may be screened for the presence and/or expression of the transgene by any suitable method. Screening is often accomplished by Southern blot or Northern blot analysis, using a probe that is complementary to at least a portion of the transgene. Western blot analysis using an antibody against the protein encoded by the transgene may be employed as an alternative or additional method for screening for the presence of the transgene product. Typically, DNA is prepared from tail tissue and analyzed by Southern analysis or PCR for the transgene. Alternatively, the tissues or cells believed to express the transgene at the highest levels are tested for the presence and expression of the transgene using Southern analysis or PCR, although any tissues or cell types may be used for this analysis.

Alternative or additional methods for evaluating the presence of the transgene include, without limitation, suitable biochemical assays such as enzyme and/or immunological assays, histological stains for particular marker or enzyme activities, flow cytometric analysis, and the like. Analysis of the blood may also be useful to detect the presence of the transgene product in the blood, as well as to evaluate the effect of the transgene on the levels of various types of blood cells and other blood constituents.

Progeny of the transgenic animals may be obtained by mating the transgenic animal with a suitable partner, or by in vitro fertilization of eggs and/or sperm obtained from the transgenic animal. Where mating with a partner is to be performed, the partner may or may not be transgenic and/or a knockout; where it is transgenic, it may contain the same or a different transgene, or both. Alternatively, the partner may be a parental line. Where in vitro fertilization is used, the fertilized embryo may be implanted into a surrogate host or incubated in vitro, or both. Using either method, the progeny may be evaluated for the presence of the transgene using methods described above, or other appropriate methods.

The transgenic animals produced in accordance with the present invention will include exogenous genetic material.

Further, in such embodiments the sequence will be attached to a transcriptional control element, e.g., a promoter, which preferably allows the expression of the transgene product in a specific type of cell.

Retroviral infection can also be used to introduce the transgene into a non-human animal. The developing non-human embryo can be cultured in vitro to the blastocyst stage. During this time, the blastomeres can be targets for retroviral infection (Jaenich, R. (1976) *PNAS* 73:1260–1264). Efficient infection of the blastomeres is obtained by enzymatic treatment to remove the zona pellucida (*Manipulating the Mouse Embryo*, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927–6931; Van der Putten et al. (1985) PNAS 82:6148–6152). Transfection is easily and efficiently obtained by culturing the blastomeres on a monolayer of virus-producing cells (Van der Putten, supra; Stewart et al. (1987) *EMBO J.* 6:383–388). Alternatively, infection can be performed at a later stage. Virus or virus-producing cells can be injected into the blastocoele (Jahner et al. (1982) *Nature* 298:623–628). Most of the founders will be mosaic for the transgene since incorporation occurs only in a subset of the cells which formed the transgenic non-human animal. Further, the founder may contain various retroviral insertions of the transgene at different positions in the genome which generally will segregate in the offspring. In addition, it is also possible to introduce transgenes into the germ line by intrauterine retroviral infection of the midgestation embryo (Jahner et al. (1982) supra).

A third type of target cell for transgene introduction is the embryonal stem cell (ES). ES cells are obtained from pre-implantation embryos cultured in vitro and fused with embryos (Evans et al. (1981) *Nature* 292:154–156; Bradley et al. (1984) *Nature* 309:255–258; Gossler et al. (1986) PNAS 83:9065–9069; and Robertson et al. (1986) *Nature* 322:445–448). Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal. For review see Jaenisch, R. (1988) *Science* 240:1468–1474.

4.5 Methods of Treatment
4.5.1. Effective Dose

Toxicity and therapeutic efficacy of such compounds can be determined by standard pharmaceutical procedures in cell cultures or experimental animals, e.g., for determining The $LD_{50}$ (the dose lethal to 50% of the population) and the $Ed_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

4.5.2. Formulation and Use

Pharmaceutical compositions for use in accordance with the present invention may be formulated in a conventional manner using one or more physiologically acceptable carriers or excipients. Thus, the compounds and their physiologically acceptable salts and solvates may be formulated for administration by, for example, injection, inhalation or insufflation (either through the mouth or the nose) or oral, buccal, parenteral or rectal administration.

For such therapy, the compounds of the invention can be formulated for a variety of loads of administration, including systemic and topical or localized administration. Techniques and formulations generally may be found in Remmington's Pharmaceutical Sciences, Meade Publishing Co., Easton, Pa. For systemic administration, injection is preferred, including intramuscular, intravenous, intraperitoneal, and subcutaneous. For injection, the compounds of the invention can be formulated in liquid solutions, preferably in physiologically compatible buffers such as Hank's solution or Ringer's solution. In addition, the compounds may be formulated in solid form and redissolved or suspended immediately prior to use. Lyophilized forms are also included.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., ationd oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. Other suitable delivery systems include microspheres which offer the possibility of local noninvasive delivery of drugs over an extended period of time. This technology utilizes microspheres of precapillary size which can be injected via a coronary catheter into any selected part of the e.g. heart or other organs without causing inflammation or ischemia. The administered therapeutic is slowly released from these microspheres and taken up by surrounding tissue cells (e.g. endothelial cells).

Systemic administration can also be by transmucosal or transdermal means. For transmucosal or transdernal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays or using suppositories. For topical administration, the oligomers of the invention are formulated into ointments, salves, gels, or creams as generally known in the art. A wash solution can be used locally to treat an injury or inflammation to accelerate healing.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The present invention is further illustrated by the following examples which should not be construed as limiting in any way. The contents of all cited references (including literature references, issued patents, published patent applications as cited throughout this application) are hereby expressly incorporated by reference.

The practice of the present invention will employ, unless otherwise indicated, conventional techniques that are within the skill of the art. Such techniques are explained fully in the literature. See, for example, Molecular Cloning A Laboratory Manual, (2nd ed., Sambrook, Fritsch and Maniatis, eds., Cold Spring Harbor Laboratory Press: 1989); DNA Cloning, Volumes I and II (D. N. Glover ed., 1985); Oligonucleotide Synthesis (M. J. Gait ed., 1984)

EXAMPLE 1

Genetic Linkage of a Macular Degeneration Causing Gene to the Short Arm of Human Chromosome 2

A total of 86 family members at 50% risk for autosomal dominant radial drusen were studied (FIG. 1). These individuals belonged to four families that were known to be related. Genealogical investigation revealed that family A has lived in the United States since at least the late 1700's. The two branches of this family (A1 and A2) were found to be connected by a sibship that lived in West Virginia in the 1790's. Families B–D all originated from the Leventine valley of southern Switzerland. Members of family B have been the subjects of previous reports by Vogt,[23] Klainguti,[24] Forni and Babel,[26] and Scarpatetti, Forni, and Niemeyer.[31]

Informed consent was obtained from study participants. Seventy-one patients had complete eye examinations (visual acuity, slit lamp examination, indirect ophthalmoscopy and retinal biomicroscopy). The medical records and fundus photographs of 15 additional patients were reviewed. Throughout the study, the clinicians remained masked to the evolving genotypic data. Patients were judged to be affected if: 1) they were found to have unmistakable evidence of radial drusen on clinical examination; or, 2) if they were found to have large disciform scars but had children affected with radial drusen. Blood samples were obtained from all of the affected family members as well as 19 spouses of affected patients with children. Seven to ten milliliters of blood were obtained from each patient in EDTA-containing glass tubes. DNA was prepared from the blood using a non-organic method.[32] Oligonucleotide primers complementary to sequences flanking 380 short tandem repeat polymorphisms (STRPs) distributed across the entire autosomal genome were obtained from Research Genetics (Marker Sets 6 and 6A). The majority of these STRPs were tetranucleotide repeat polymorphisms developed by the Cooperative Human Linkage Center (CHLC).[33] Fifty nanograms of each patients DNA were used as template in a 8.35 $\mu$l polymerase chain reaction (PCR) containing 1.25 $\mu$l 10$\chi$ buffer (100 mM Tris-HCL pH 8.8, 500 mM KCl, 15 mM MgCl2, 0.01% w/v gelatin, 200 $\mu$m of each dCTP, dATP, dGTP and dTTP, 1 pmole of each primer and 0.25U Taq polymerase (Perkin-Elner Cetus). Samples were incubated in a DNA thermocycler (Omnigene) for 35 cycles under the following conditions; 94° C. for 30 sec, 55° C. for 30 sec, 72° for 30 sec. After amplification, 5 $\mu$l of stop solution (95% formamide, 10 mM NaOH, 0.05% Bromophenol Blue, 0.05% Xylene Cyanol) were added to each sample. Amplification products were then denatured and electrophoresed on 6% polyacrylamide gels at 60W for approximately 3 hours. Following electrophoresis, gels were silver stained as previously described.[34,35] Permanent records were created by placing a sheet of Silver Sequence film (Promega) against the dried gel and placing it on a light box for 5–9 sec. The film was then processed in Dektol developer.

Because of the variable expressivity of the disease, only affected patients and informative spouses were included in the linkage analysis. Pairwise linkage analysis was performed with the MLINK and LODSCORE programs as implemented in the FASTLINK (v2.3) version[36,37] of the LINKAGE program package.[38] Multipoint linkage of three markers (D2S337, D2S378 and D2S119) and the disease locus was performed with the fast version of LINKMAP from FASTLINK (v2.3). The distances between the three markers were held fixed while the disease locus was moved through the map. The genetic maps used for the multipoint analysis and analysis of recombinants were constructed in the following manner. Genotypic data from the CEPH reference panel were obtained electronically from two primary sources: CEPH (ftp.cephb.fr) and CHLC (ftp.chlc.org). The potential informativeness of each marker in the CEPH reference panel was estimated by conducting pairwise linkage analysis of each marker against itself using the CLODSCORE module of the LINKAGE (v5.1) package. The two most informative markers were used as the ordered loci for a CRI-MAP BUILD run (CRI-MAP v2.2).[39] Markers were then incorporated into the map in decreasing order of informativeness. The map building process continued until no further markers could be placed into the map while retaining a predetermined level of significance over the next most likely order. To obtain an order with a high level of confidence for the multipoint analysis of the disease locus, odds of at least $10^8$ to 1 were required. The map used to place the recombination events within the families was constructed with odds of $10^3$ to 1. Markers that could not be incorporated into the map with at least 10 to 1 odds were placed into the map in a location most consistent with the observed recombinants. For the data given in FIG. 3, the allele frequencies were assumed to be equal for each marker. The true population allele frequencies for each marker could not be reliably estimated from the small number of spouses in the families. In order to show that the assumption of the equal allele frequencies would not significantly affect the linkage results, the lod scores were calculated using allele frequencies for the "affected" allele of two of the most tightly linked markers (GATA26H01 and D2S378) ranging from 0.01 to 0.5. In family A alone, the Zmax remained greater than 4 for each of these markers for all allele frequencies in this range. In the six spouses of family A that were studied, the frequency of the "affected" allele of GATA26H01was 16% and for D2S378 was 0%.

Results

Fifty-six patients were found to have fundus abnormalities consistent with the diagnosis of autosomal dominant radial drusen. The affected patients ranged in age from 15 to 85 years. Most were asymptomatic until the fourth or fifth decade, at which point they began experiencing a variety of symptoms including decreased visual acuity (especially after moving from a brightly lit room to a dim one), paracentral scotomas, photophobia and metamorphopsia. The visual acuity of most patients declined steadily between the ages of 50 and 80 such that the median visual acuity in affected patients between 70 and 79 years of age was less than 20/200 (FIG. 2).

Linkage of radial drusen of 2 p was first suspected when all 29 affected individuals from family A were found to share a common allele of marker D2S1352. Genotyping of all 4 families with 18 different STRPs that map to 2 p revealed significant linkage (lod>3.0) in family A with 14 different markers and in family B with two different markers (D2S391 and GATA26H10). The maximum lod score observed in a single family was 7.0 (theta=0) and was obtained with marker D2S378 in family A. The maximum lod score obtained by combining all 4 families was 10.5 (theta=0) and was obtained with marker D2S378. The lod scores obtained with 18 different chromosome 2 markers are given in FIG. 3. The analysis of patients who exhibited recombination events near the linked interval is also shown in FIG. 3. These recombination events show the disease-causing gene to lie within the 14 cM interval between markers D2S1761 (telomeric) and D2S444 (centromeric).

Multipoint analysis was performed with the genotypic data from three markers D2S337, D2S378 and D2S119) pooled from all four families. This analysis revealed a peak lod score of 12, centered on marker D2S378. The lod-1 confidence interval[40] was 8 cM.

Table 2 shows the set of marker alleles (haplotype) linked to the disease phenotype in each of the four families. For all nine markers in the linked interval, the two main branches of family A were found to have the same allele linked to the disease phenotype. In contrast, none of the three Swiss families (B–D) showed this degree of haplotypic similarity with each other, or with family A.

TABLE 2

| Marker | Alleles* linked to disease phenotype | | | | |
|---|---|---|---|---|---|
| | Families | | | | |
| (alleles)** | A1 | A2 | B | C | D |
| D2S391 (5) | 2 | 2 | 1 | 2 | 2 |
| D2S123 (6) | 6 | 6 | 5 | 6 | 1 |
| D2S1352 (4) | 3 | 3 | 4 | 3 | 3 |
| GATA26H10 (10) | 4 | 4 | 7 | 7 | 3 |
| D2S378 (7) | 3 | 3 | 4 | 3 | 4 |
| D2S1364 (5) | 5 | 5 | 5 | 5 | 5 |
| D2S357 (7) | 5 | 5 | 2 | 5 | 5 |
| D2S370 (6) | 4 | 4 | 3 | 3 | 4 |

*For each marker, the allele with the greatest number of repeats is designated as allele 1.
**The number in parentheses is the total number of different alleles observed in the four families in this study.

Analysis of observed recombination events in affect individuals has refined the interval containing the disease gene to the genomic segment between markers D2S2153 and D2S357 (see FIG. 1). This interval has been further narrowed by the identification of a segment of the genome that is shared between a set of malattia leventinese families that live in the Leventine Valley of Switzerland. This analysis is capable of identifying recombination events that occurred many years ago in the common ancestors that link these families. This shared segment analysis suggests that the disease gene lies within the interval bounded by markers D2S2153 and D2S378 (see FIG. 1).

Within the candidate interval noted above, a group of genes exist that have some additional reason or reasons to implicate them as the disease-causing gene in malattia leventinese patients. These genes include: WI-16857, Wi-12526 (B-fodrin), WI-15186, WI-8771 (S1-5), WI-6704, WI-6613, WI-6241, SGC-34452, stSG-42480, WI-18292, SGC-31346, WI-11399.

EXAMPLE 2

Identification of WI-8771 (S1-5) (FBNL) as the Macular Degeneration Causing Gene The Assay A limitation to the assay of the above genes for mutations has been the paucity of available in formation about the genomic structure and genomic sequence of these genes. Thus, many assays have been limited to selected regions of the coding sequence 20 or more base pairs away from intron-exon boundaries. Because of these limitations, negative screening results have been difficult to interpret (because true disease-causing mutations could be located in the unscreened regions of the genes).

Work was thus directed to identifying the genomic structure and genomic sequence of the most promising candidate genes, so that more complete assays could be developed. It was found that aportion of the s1-5(FBNL) gene (Genebank Accession U03877—SEQ. ID. No. 1). The relevant portion is exon 10 inclusive of previously unpublished intronic s equenc e (SEQ. ID. No. 2). The availability of this new intronic sequence permitted the design of specific primers (SEQ. ID. Nos. 3 and 4) for amplification and mutation screening of the entire cod ing sequence of exon 10 of this gene.

The Gene (S1-5 also Known as FBNL)

Lecka-Czernik et al (1995) isolated an overexpressed cDNA sequence (S1-5) from human fibroblasts from a patient with Werner syndrome. They noted S1-5 codes for a novel protein containing epidermal growth factor like domains (EGF). They matched the con sensus sequences with several known extracellular domains that play a r ole in cell growth, development and cell signalling. They found 5–6 EGF domai ns present depending o n translational start site. There is significant similarity between this gene and transforming growth factor beta 1 binding protein as well as the following extracellular matrix proteins: Fibulin, Fibrillin, Nidogen, Notch (in Drosophila homologs in human), Protein S, and Factor IX. All of these proteins are secreted into the extracellular space or bind to the plasma membrane and interact with other proteins. S1-5 has a signal peptide, EGF domains, and an N glycosylation site suggesting it is an extracellular factor involved in cell proliferation.

Ikegawa et al (1996) determined the genomic organization of S1-5. They showed that it spans 18 kb of genomic DNA and maps to 2p16. They demonstrated abundant expression in all tissues studied except brain and peripheral lymphocytes. They showed that this gene is highly homologous to fibrillin, and in fact the approved symbol for S1-5 is now FBNL (fibrillin like). The gene has 12 exons but the first 3 exons are in the 5' UTR. Ikegawa et al did define the intron exon boundaries but did not provide enough intronic sequence to make primers for screening the entire coding sequence of the exons.

Mutation Screening

The exon 10 screening assay was used to screen 34 unrelated nuclear families (113 affected patients) affected with malattia leventinese for mutations in exon 10 of the s 1-5 gene. Twenty-one of these families were known by haplotype analysis to be related to one another (the Swiss group), and as were two additional families from the US. Thirteen of the families had no geographic or haplotypic information to link them. Screening of exon 10 of the S1-5 gene in these families revealed the same heterozygous sequence variation in every affected member of every family in our collection (all 113 patients). This sequence variation altered the first nucleotide of codon 345 from a C to a T and would be expected to change the amino acid at this position from arginine to tryptophan (a basic to an uncharged amino acid).

Screening of 383 control patients (190 from Iowa, 93 from Australia and 93 from Switzerland) revealed only a single heterozygous occurrence of this change and that was in a patient from the Italian-speaking region of Switzerland near the Leventine valley.

Screening of 500 unrelated age-related macular degeneration patients for mutations in this exon revealed only a single patient with this sequence change.

Interpretation

This Arg345Trp mutation in the S1-5 gene on chromosome 2p is therefor likely to be the cause of the specific form of human macular degeneration known as malattia leventinese or "radial drusen" and potentially other macular degenerations.

Significance

Only a portion of the S1-5 gene has been screened in human macular degeneration patients at this time—and it is possible that other mutations elsewhere in this gene will prove to be responsible for a subset of typical age related macular degeneration. The S1-5 gene is a member of a gene family with at least 2 other members (i.e. fibulin 1 and fibulin 2). Mutations in these other genes therefore are likely to cause a subset of macular degeneration. The specific Arg345Trp mutation is in a domain of the molecule with homology to epidermal growth factor and this observation may contribute to the elucidation of the mechanism of drusen formation. At the very least, knowledge of this specific drusen-causing mutation will allow an animal model of human macular degeneration to be developed with transgenic technology as described herein.

EXAMPLE 3

Identification of an Additional Mutation in WI-8771 (S1-5) (FBNL)

As described above, all 37 families (162 affected patients) studied had an exon 10 shift on SSCP that looked identical. All of the families were then sequenced to make sure that it was all the same mutation. All of the families sequenced had the Arg345Trp mutation found in the original patients. However, the sequence of one Swiss patient came back and had a different amino acid changing mutation in exon 10: namely, Arg362Gln. This mutation, therefore, could be responsible for Doyne's dystrophy, while the Arg345Trp mutation is responsible for the malatia leventinese form of age related macular degeneration.

```
S1-5 Sequence from GeneBank (Accession U03877)

CAATGCACTG ACGGATATGA GTGGGATCCT GTGAGACAGC AATGCAAAGA

TATTGATGAA TGTGACATTG TCCCAGACGC TTGTAAAGGT GGAATGAAGT

GTGTCAACCA CTATGGAGGA TACCTCTGCC TTCCGAAAAC AGCCCAGATT

ATTGTCAATA ATGAACAGCC TCAGCAGGAA ACACAACCAG CAGAAGGAAC

CTCAGGGCA ACCACCGGGG TTGTAGCTGC CAGCAGCATG GCAACCAGTG

GAGTGTTGCC CGGGGGTGGT TTTGTGGCCA GTGCTGCTGC AGTCGCAGGC

CCTGAAATGC AGACTGGCCG AAATAACTTT GTCATCCGGC GGAACCCAGC
```

-continued

```
TGACCCTCAG CGCATTCCCT CCAACCCTTC CCACCGTATC CAGTGTGCAG

CAGGCTACGA GCAAAGTGAA CACAACGTGT GCCAAGACAT AGACGAGTGC

ACTGCAGGGA CGCACAACTG TAGAGCAGAC CAAGTGTGCA TCAATTTACG

GGGATCCTTT GCATGTCAGT GCCCTCCTGG ATATCAGAAG CGAGGGGAGC

AGTGCGTAGA CATAGATGAA TGTACCATCC CTCCATATTG CCACCAAAGA

TGCGTGAATA CACCAGGCTC ATTTTATTGC CAGTGCAGTC CTGGGTTTCA

ATTGGCAGCA AACAACTATA CCTGCGTAGA TATAAATGAA TGTGATGCCA

GCAATCAATG TGCTCAGCAG TGCTACAACA TTCTTGGTTC ATTCATCTGT

CAGTGCAATC AAGGATATGA GCTAAGCAGT GACAGGCTCA ACTGTGAAGA

CATTGATGAA TGCAGAACCT CAAGCTACCT GTGTCAATAT CAATGTGTCA

ATGAACCTGG GAAATTCTCA TGTATGTGCC CCCAGGGATA CCAAGTGGTG

AGAAGTAGAA CATGTCAAGA TATAAATGAG TGTGAGACCA CAAATGAATG

CCGGGAGGAT GAAATGTGTT GGAATTATCA TGGCGGCTTC CGTTGTTATC

CACGAAATCC TTGTCAAGAT CCCTACATTC TAACACCAGA GAACCGATGT

GTTTGCCCAG TCTCAAATGC CATGTGCCGA GAACTGCCCC AGTCAATAGT

CTACAAATAC ATGAGCATCC GATCTGATAG GTCTGTGCCA TCAGACATCT

TCCAGATACA GGCCACAACT ATTTATGCCA ACACCATCAA TACTTTTCGG

ATTAAATCTG GAAATGAAAA TGGAGAGTTC TACCTACGAC AAACAAGTCC

TGTAAGTGCA ATGCTTGTGC TCGTGAAGTC ATTATCAGGA CCAAGAGAAC

ATATCGTGGA CCTGGAGATG CTGACAGTCA GCAGTATAGG GACCTTCCGC

ACAAGCTCTG TGTTAAGATT GACAATAATA GTGGGGCCAT TTTCATTTTA

GTCTTTTCTA AGAGTCAACC ACAGGCATTT AAGTCAGCCA AGAATATTG

TTACCTTAAA GCACTATTTT ATTTATAGAT ATATCTAGTG CATCTACATC

TCTATACTGT ACACTCACCC ATAACAAACA ATTACACCAT GGTATAAAGT

GGGCATTTAA TATGTAAAGA TTCAAAGTTT GTCTTTATTA CTATATGTAA

ATTAGACATT AATCCACTAA ACTGGTATTA TTCAAGAGAG CTAAGTATAC

ACTATCTGGT GAAACTTGGA TTCTTTCCTA TAAAAGTGGG ACCAAGCAAT

GATGATCTTC TGTGGTGCTT AAGGAAACTT ACTAGAGCTC CACTAACAGT

CTCATAAGGA GGCAGCCATC ATAACCATTG AATAGCATGC AAGGGTAAGA

ATGAGTTTTT AACTGCTTTG TAAGAAAATG GAAAAGGTCA ATAAAGATAT

ATTTCTTTAG AAAATGGGGA TCTGCCATAT TTGTGTTGGT TTTTATTTTC

ATATCCAGCC TAAAGGTGGT TGTTTATTAT ATAGTAATAA ATCATTGCTG

TACAACATGC TGGTTTCTGT AGGGTATTTT TAATTTGTC AGAAATTTTA

GATTGTGAAT ATTTTGTAAA AAACAGTAAG CAAAATTTTC CAGAATTCCC

AAAATGAACC AGATACCCCC TAGAAAATTA TACTATTGAG AAATCTATGG

GGAGGATATG AGAAAATAAA TTCCTTCTAA ACCACATTGG AACTGACCTG

AAGAAGCAAA CTCGGAAAAT ATAATAACAT CCCTGAATTC AGGCATTCAC

TTCTAAGTAA AATTTAAATC CTAACACTTC ACTAATTTAT AACTAAAATT

TCTCATCTTC GTACTTGATG CTCACAGAGG AAGAAAATGA TGATGGTTTT

TATTCCTGGC ATCCAGAGTG ACAGTGAACT TAAGCAAATT ACCCTCCTAC
```

```
                                -continued
CCAATTCTAT GGAATATTTT ATACGTCTCC TTGTTTAAAA TCTGACTGCT

TTACTTTGAT GTATCATATT TTTAAATAAA AATAAATATT CCTTTAGAAG

ATCACTCTAA AASequence 2

Exon 10 with a portion of Intron 10 (Seq. Id. No. 2)

ATATAAATGA GTGTGAGACC ACAAATGAAT GCCGGGAGGA TGAAATGTGT

TGGAATTATC ATGGCGGCTT CCGTTGTTAT CCACGAAATC CTTGTCAAGAT

CCCTACATT CTAACACCAG AGAAGTAAGAAAAATCAGAACTTTTGAAAGTG

AGGATTTTCTGGTCTTACCAAGCCAAACTGCTGAATACTTTTGTTTGTCTCTG

CAG

Exon 10 primers

10 Foward

5'AAATGATGTGAGACCACAAA3' (SEQ ID NO. 3)

10 Reverse

5'ATTCAGCAGTTTGGCTTGGT3' (SEQ ID NO. 4).
```

Equivalents

Those skilled in the art will recognize, or be able to ascertain using no more than routine experimentation, many equivalents of the specific embodiments of the invention described herein. Such equivalents are intended to be encompassed by the following claims.

REFERENCES

1) Best F. Uber eine hereditare maculaaffektion: Bietrage zur vererbungslehre. *Z Augenheilkd.* (1905); Vol. 13: pp. 199–212.
2) Sorsby A, Joll Mason M E, Gardener N. A findus dystrophy with unusual features. *Br J. Opthalmol.* (1949); Vol. 33: pp. 67–97.
3) Stargardt K. Ueber familiare, progressive degeneration in der makulagegend des auges. *Albrecht Von Graefes Arch Klin Exp Opthalmol.* (1909); Vol. 71, pp. 534–550.
4) Ferrell R E, Mintz-Hittner H., Antoszyk J H. Linkage of atypical vitelliform macular dystrophy (VDM-1) to the soluble glutamate pyruvate transaminase (GPT1) locus. *Am J Hum Genet.* (1983); Vol. 35; pp 78–84.
5) Jacobson D M, Thompson H S, Bartley J A. X-linked progressive cone dystrophy. *Ophthalmology*, (1989); Vol. 96; pp. 885–895.
6) Small K W, Weber J L, Roses A, et al. North Carolina macular dystrophy is assigned to chromosome 6. *Genomics* (1992) Vol. 13; pp. 681–685.
7) Stone E M, Nichols B E, Streb L M, Kimura A E, Sheffield V C. Genetic linkage of vitelliform macular degeneration (Best's disease) to chromosome 11q13. *Nature Genet.* (1992); Vol. 1: pp. 246–250.
8) Forsman K, Graff C, Nordstrom S, et al. The gene for Best's macular dystrophy is located in 11q13 in a Swedish family. *Clin Genet.* (1992); Vol. 42: pp. 156–159.
9) Kaplan J S, Gerber S, Lavget-Piet D, et al. A gene for Stargardt's disease (fundus flavimaculatus) maps to the short arm of chromosome 1, *Nature Genet.* (1993) Vol. 5: pp. 308–311.
10) Stone E M, Nichols B E, Kimura A E, et al. Clinical features of a Stargardt-like dominant progressive macular dystrophy with genetic linkage to chromosome 6q. *Arch Opthalmol.* (1994); Vol. 112: pp. 763–772.
11) Zhang K, Bither P P, Park R, et al. A dominant Stargardt's macular dystrophy locus maps to chromosome 13q34. *Arch Opthalmol.* (1994); Vol. 112: pp. 759–764.
12) Evans K, Fryer A, Ingelhearn C, et al. Genetic linkage of cone-rod retinal distropy to chromosome 19q and evidence for segregation distortion. *Nature Genet.* (1994); Vol.6: pp.210–213.
13) Kremer H, Pinckers A, vandenHelm B, et al. Localization of the gene for dominant cystoid macular dystrophy on chromosome 7p. *Hum Mol Genet*, (1994); Vol. 3: pp. 299–302.
14) Kelsell R E, Godley B F, Evans K, et al. Localization of the gene for progressive bifocal chorioretinal atrophy (PBCRA) to chromosome 6q. *Hum Mol Genet.* (1995); Vol 4: pp. 1653–1656.
15) Nathans J, Davenport C M, Maumenee I H, et al. Molecular genetics of human blue cone monochromacy. *Science.* (1989); Vol 245: pp. 831–838.
16) Wells J, Wroblewski J., Keen J. Mutations in the human retinal degeneration slow (RDS) gene can cause either retinitis pigmentosa or macular dystrophy. *Nature Genet.* (1993); Vol. 3: pp. 213–218.
17) Nichols B E, Sheffield V C, Vandenburgh K. Butterfly-shaped pigment dystrophy of the fovea is caused by a point mutation in codon 167 of the RDS gene. *Nature Genet.* (1993a); Vol. 3: pp. 202–207.
18) Weber B H F, Vogt G, Pruett R C, Stohr H, Felbor U. Mutations in the tissue inhibitor of metalloproteinases-3 (TIMP3) in patients with Sorsby's fundus dystrophy. *Nature Genet.* (1994): Vol. 8: pp. 352–355.
19) Leibowitz H., Krueger D E, Maunder L R, et al. The Framingham Eye Study Monograph; an ophthalmological and epidemiological study of cataract, macular degeneration, diabetic retinopathy, macular degeneration and visual acuity in a general population of 2,631 adults, (1973–75) *Survey of Opthalmol.* (1980); Vol. 24: (Suppl.): pp. 335–610.
20) Hutchinson J, Tay W. Symmetrical central choroidoretinal disease occurring in senile persons. *R. London Opthalmol Hosp. Rep.* (1875) Vol. 8: pp. 231–244.
21) Doyne R W. Peculiar condition of choroiditis occurring in several members of the same family. *Trans. Opthal. Soc. U. K.* (1899); Vol. 19: p. 71.

22) Collins T. A pathological report upon a case of Doyne's chorioditis ("honeycomb" or "family choroiditis"). *Ophthalmoscope* (1913); Vol. 11: pp. 537–538.
23) Vogt A. Die Opthalmoskopie im rotfreien Licht. *Graefe Saemisch Handb. d. Ges. Augenheilkd*, 3d ed. Berlin, Springer, (1925); Vol. 3: pp. 1–118.
24) Klainguti, R. Die tapeto-retinale Degeneration im Kanton Tessin (Schweiz. Opthal. Ges. 25/26-6-1932, Biel.); ref.: *Z. Augenheilkd*, 82–83, 1932; *Klin. Monattsbl. Augenheilkd*. (1932); Vol. 107: pp. 361–372.
25) Waardenburg P. J. On macula-degeneration. *Opthalmologica*. (1948); Vol. 115: pp. 115–116.
26) Forni S, Babel J. _tude clinique et histologique de la malattia leventinse. Affection apparetnant au groupe des d_g_n_rescences hyalines du p_le post_rieur. *Opthalmologica*. (1962); Vol. 143: pp. 313–322.
27) Piguet B, Haimovici R, Bird A C. Dominantly inherited drusen represent more than one disorder: a historical review. *Eye* (1995); Vol. 9: pp. 34–41.
28) Streicher T, Kremery K. Das fluoreszenzangiographische Bild der heredit_ren Drusen. Klin. *Monatsbl. Augenheilkd*. (1976); Vol. 169: pp. 22–30.
29) Dusek J, Streicher T, Schmidt K. Heredit_re Drusen der Bruchschen Membran I. Klinische und lichtmikroskopische Beobachtungen. *Klin. Monatsbl. Augenheilkd*. (1982); Vol. 181: pp. 27–31.
30) Gass J D M. Diseases causing choroidal exudative and hemorrahagic localized (disciform) detachment of the retina and pigment epithelium. *Stereoscopic Atlas of Macular Diseases*, C. V. Mosby Co., St. Louis. (1987); Vol. 3: pp. 96–97.
31) Scarpatetti A., Forni S., Neimeyer G. Die Netzhautfunktion bei Malattia leventinese (dominant drusen). *Klinische Monatsblatter fur Augenheilkunde*. (1978); Vol. 4: pp. 590–7.
32) Buffone G J, Darlington G J. Isolation of DNA from biological specimens without extraction with phenol. *Clin. Chem*. (1985); Vol. 31: pp.164–165.
33) Sheffield, V. C., Weber, J. L., Buetow, K. L., et al., A Collection of tri and tetranucleotide repeat markers used to generate high quality, high resolution human genome-wide linkage maps, *Human Molecular Genetics*, in press.
34) Bassam B J, Caetano-Anolles G., Gresshoff P M. Fast and sensitive silver staining of DNA in polyacrylamide gels. *Anal Biochem*. (1991); Vol. 196; pp. 80–83.
35) Nichols B E, Bascom R., Litt M., et al. Refining the locus for Best's vitelliform macular dystrophy and mutation analysis of the candidate gene ROM1. *Am J Hum. Genet*. (1994); Vol. 54: pp. 95–103.
36) Cottingham Jr. R W, Idury R M, Schaffer A A. Faster sequential genetic linkage computations. *Am J Hum Genet*. (1993); Vol 53: pp. 252–263.
37) Schaffer A A, Gupta S K, Shriram K, Cottingham Jr. R W. Avoiding recomputation in genetic linkage analysis. *Hum Hered*. (1994); Vol. 44: pp. 225–237.
38) Lathrop G M, Lalouel J M. Easy calculations of lod scores and genetic risks on small computers. *Am. J Hum. Genet*. (1984); Vol. 36: pp. 460–465.
39) Donis-Keller H, Green P., Helms C. et al. A Genetic linkage map of the human genome. *Cell*. (1987); Vol. 51: pp. 319–337.
40) Conneally P. M., Edwards J. H., Kidd K K, et al. Report of the committee on methods of linkage analysis and reporting. *Cytogenet. Cell Genet*. (1985); Vol. 40: pp. 356–359.
41) Gass J D M. Drusen and disciform macular detachment and degeneration. Arch *Opthalmol*. (1973); Vol. 90: pp. 206–217.
42) Hyman L G, Lilienfeld A M, Ferris F L, Fine S L. Senile macular degeneration: A case-control study. *Am J Epidemiol*. (1983); Vol. 118: pp. 213–227.
43) Heiba I M, Elston R C, Klein B E K, Klein R. Sibling correlations and segregation analysis of age-related maculopathy: the Beaver Dam Eye Study. *Genet. Epidemiol*. (1994); Vol. 11: pp. 51–67.
44) Hu R J, Watanabe M, Bennett V. Characterization of human brain cDNA encoding the general insoform of B-spectrin. *J Biolog. Chem*. (1992); Vol. 267: pp. 18715–18722.
45) Chang J G, Scarpa A, Eddy R L, et al. Cloning of a portion of the chromosomal gene and cDNA for human B-fordin, the nonerythroid form of B-spectrin. *Genomics*, (1993); Vol. 17: pp. 287–293.
46) Travis G, Sutcliffe J, Bok D. The retinal digeneration slow (rds) gene product is a photoreceptor disc membrane-associated glycoprotein. Neuron (1991); Vol. 6: pp. 61–70.
47) Bascom R A, Schappert K, McInnes R R. Cloning of the human and murine ROM 1 genes: genomic organization and sequence conservation. *Hum Molec Genet*. (1993); Vol. 2: pp. 385–391.

What is claimed is:

1. An isolated nucleic acid comprising (i) a nucleotide sequence which is identical to SEQ ID NO:1, except that nucleotide 952 is a thymidine, (ii) a nucleotide sequence which is identical to SEQ ID NO:2, except that nucleotide 33 is a thymidine, or (iii) a complement of the sequence set forth in (i) or (ii).

2. An isolated nucleic acid comprising at least 20 consecutive nucleotides of (i) a nucleotide sequence which is identical to SEQ ID NO:1, except that nucleotide 952 is a thymidine and wherein the nucleic acid includes nucleotide 952, (ii) a nucleotide sequence which is identical to SEQ ID NO:2, except that nucleotide 33 is a thymidine and wherein the nucleic acid includes nucleotide 33, or (iii) a complement of the sequence set forth in (i) or (ii).

3. A cell comprising an isolated nucleic acid, comprising the nucleotide sequence set forth in SEQ ID NO: 2, or a complement thereof.

4. An isolated nucleic acid that encodes a polypeptide, comprising a nucleotide sequence which is identical to SEQ ID NO:1, except that nucleotide 952 is a thymidine.

5. A cell comprising the nucleic acid of claim 4.

6. A cell comprising the nucleic acid of claim 1.

* * * * *

SEQUENCE LISTING

```
<160> NUMBER OF SEQ ID NOS:   4

<210> SEQ ID NO 1
<211> LENGTH: 2512
<212> TYPE: DNA
<213> ORGANISM: Homo sapiens

<400> SEQUENCE: 1
caatgcactg  acggatatga  gtgggatcct  gtgagacagc  aatgcaaaga  tattgatgaa      60
tgtgacattg  tcccagacgc  ttgtaaaggt  ggaatgaagt  gtgtcaacca  ctatggagga     120
tacctctgcc  ttccgaaaac  agcccagatt  attgtcaata  atgaacagcc  tcagcaggaa     180
acacaaccag  cagaaggaac  ctcaggggca  accaccgggg  ttgtagctgc  cagcagcatg     240
gcaaccagtg  gagtgttgcc  cggggtggt   tttgtggcca  gtgctgctgc  agtcgcaggc     300
```

-continued

```
cctgaaatgc agactggccg aaataacttt gtcatccggc ggaacccagc tgaccctcag    360
cgcattccct ccaaccttc ccaccgtatc cagtgtgcag caggctacga gcaaagtgaa    420
cacaacgtgt gccaagacat agacgagtgc actgcaggga cgcacaactg tagagcagac    480
caagtgtgca tcaatttacg gggatccttt gcatgtcagt gccctcctgg atatcagaag    540
cgaggggagc agtgcgtaga catagatgaa tgtaccatcc ctccatattg ccaccaaaga    600
tgcgtgaata caccaggctc atttttattgc cagtgcagtc ctgggtttca attggcagca    660
aacaactata cctgcgtaga tataaatgaa tgtgatgcca gcaatcaatg tgctcagcag    720
tgctacaaca ttcttggttc attcatctgt cagtgcaatc aaggatatga gctaagcagt    780
gacaggctca actgtgaaga cattgatgaa tgcagaacct caagctacct gtgtcaatat    840
caatgtgtca atgaacctgg gaaattctca tgtatgtgcc cccagggata ccaagtggtg    900
agaagtagaa catgtcaaga tataaatgag tgtgagacca caatgaatg ccgggaggat    960
gaaatgtgtt ggaattatca tggcggcttc cgttgttatc cacgaaatcc ttgtcaagat   1020
ccctacattc taaaccagaa gaaccgatgt gtttgcccag tctcaaatgc catgtgccga   1080
gaactgcccc agtcaatagt ctacaaatac atgagcatcc gatctgatag gtctgtgcca   1140
tcagacatct tccagataca ggccacaact atttatgcca acaccatcaa tactttcgg    1200
attaaatctg gaaatgaaaa tggagagttc tacctacgac aaacaagtcc tgtaagtgca   1260
atgcttgtgc tcgtgaagtc attatcagga ccaagagaac atatcgtgga cctggagatg   1320
ctgacagtca gcagtatagg gaccttccgc acaagctctg tgttaagatt gacaataata   1380
gtggggccat tttcattta gtctttctta agagtcaacc acaggcattt aagtcagcca   1440
aagaatattg ttaccttaaa gcactatttt atttatagat atatctagtg catctacatc   1500
tctatactgt acactcaccc ataacaaaca attacaccat ggtataaagt gggcatttaa   1560
tatgtaaaga ttcaaagttt gtctttatta ctatatgtaa attagacatt aatccactaa   1620
actggtcttc ttcaagagag ctaagtatac actatctggt gaaacttgga ttctttccta   1680
taaaagtggg accaagcaat gatgatcttc tgtggtgctt aaggaaactt actagagctc   1740
cactaacagt ctcataagga ggcagccatc ataaccattg aatagcatgc aagggtaaga   1800
atgagttttt aactgctttg taagaaaatg gaaaaggtca ataaagatat atttctttag   1860
aaaatgggga tctgccatat ttgtgttggt ttttatttt atatccagcc taaaggtggt   1920
tgtttattat atagtaataa atcattgctg tacaacatgc tggtttctgt agggtatttt   1980
taattttgtc agaaatttta gattgtgaat attttgtaaa aacagtaag caaaattttc   2040
cagaattccc aaaatgaacc agatacccc tagaaaatta tactattgag aaatctatgg   2100
ggaggatatg agaaaataaa ttccttctaa accacattgg aactgacctg aagaagcaaa   2160
ctcggaaaat ataataacat ccctgaattc aggcattcac aagatgcaga acaaaatgga   2220
taaaaggtat ttcactggag aagttttaat ttctaagtaa aatttaaatc ctaacacttc   2280
actaatttat aactaaaatt tctcatcttc gtacttgatg ctcacagagg aagaaaatga   2340
tgatggtttt tattcctggc atccagagtg acagtgaact taagcaaatt accctcctac   2400
ccaattctat ggaatatttt atcgtctcc ttgtttaaaa tctgactgct ttactttgat   2460
gtatcatatt tttaaataaa aataaatatt cctttagaag atcactctaa aa           2512
```

<210> SEQ ID NO 2
<211> LENGTH: 208
<212> TYPE: DNA
<213> ORGANISM: Homo sapiens

```
<400> SEQUENCE: 2
atataaatga gtgtgagacc acaaatgaat gccgggagga tgaaatgtgt tggaattatc      60
atggcggctt ccgttgttat ccacgaaatc cttgtcaaga tccctacatt ctaacaccag     120
agaagtaaga aaaatcagaa cttttgaaag tgaggatttt ctggtcttac caagccaaac    180
tgctgaatac ttttgtttgt ctctgcag                                        208

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 3
aaatgagtgt gagaccacaa a                                                21

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
attcagcagt ttggcttggt                                                  20
```